US010173946B2

(12) United States Patent
Du et al.

(10) Patent No.: US 10,173,946 B2
(45) Date of Patent: Jan. 8, 2019

(54) APPARATUS AND PROCESS FOR PRODUCING GASOLINE, OLEFINS AND AROMATICS FROM OXYGENATES

(71) Applicants: Bing Du, Pittstown, NJ (US); Samuel A. Tabak, Oakton, VA (US); Mitch L. Hindman, Spring, TX (US); Eric B. Shen, Great Falls, VA (US); David L. Johnson, Doylestown, PA (US); Mohsen N. Harandi, The Woodlands, TX (US); Clay R. Sutton, Pittstown, NJ (US); Lu Han, Beaumont, TX (US); Michael F. Raterman, Doylestown, PA (US); Zhongcheng Wang, Fairfax, VA (US); Samia Ilias, Somerville, NJ (US); Brett Loveless, Houston, TX (US); Stephen J. McCarthy, Center Valley, PA (US)

(72) Inventors: Bing Du, Pittstown, NJ (US); Samuel A. Tabak, Oakton, VA (US); Mitch L. Hindman, Spring, TX (US); Eric B. Shen, Great Falls, VA (US); David L. Johnson, Doylestown, PA (US); Mohsen N. Harandi, The Woodlands, TX (US); Clay R. Sutton, Pittstown, NJ (US); Lu Han, Beaumont, TX (US); Michael F. Raterman, Doylestown, PA (US); Zhongcheng Wang, Fairfax, VA (US); Samia Ilias, Somerville, NJ (US); Brett Loveless, Houston, TX (US); Stephen J. McCarthy, Center Valley, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 410 days.

(21) Appl. No.: 14/872,340

(22) Filed: Oct. 1, 2015

(65) Prior Publication Data
US 2016/0102032 A1 Apr. 14, 2016

Related U.S. Application Data

(60) Provisional application No. 62/062,423, filed on Oct. 10, 2014, provisional application No. 62/062,396, filed on Oct. 10, 2014.

(51) Int. Cl.
*C07C 1/20* (2006.01)
*B01J 8/18* (2006.01)
*B01J 8/24* (2006.01)
*C07C 2/56* (2006.01)
*C07C 2/86* (2006.01)
*B01J 8/26* (2006.01)
*B01J 8/34* (2006.01)
*C10L 1/06* (2006.01)
(Continued)

(52) U.S. Cl.
CPC ............... *C07C 1/20* (2013.01); *B01J 8/0055* (2013.01); *B01J 8/1836* (2013.01); *B01J 8/24* (2013.01); *B01J 8/26* (2013.01); *B01J 8/34* (2013.01); *C07C 2/56* (2013.01); *C07C 2/864* (2013.01); *C07C 2/865* (2013.01); *C10G 3/49* (2013.01); *C10G 3/57* (2013.01); *C10G 3/62* (2013.01); *C10L 1/06* (2013.01); *B01J 2208/0084* (2013.01); *B01J 2208/00256* (2013.01); *B01J 2208/00274* (2013.01); *B01J 2208/00893* (2013.01); *C07C 2521/16* (2013.01); *C07C 2529/40* (2013.01); *C10G 2300/4081* (2013.01); *C10G 2400/02* (2013.01); *C10G 2400/20* (2013.01); *C10G 2400/28* (2013.01); *C10G 2400/30* (2013.01); *Y02P 30/20* (2015.11); *Y02P 30/42* (2015.11)

(58) Field of Classification Search
CPC ... C07C 1/20; C07C 2521/16; C07C 2529/40; C07C 2/56; C07C 2/864; C07C 2/865; C10G 2300/4081; C10G 2400/02; C10G 2400/20; C10G 2400/28; C10G 2400/30; C10G 3/49; C10G 3/57; C10G 3/62; B01J 2208/00256; B01J 2208/00274; B01J 2208/0084; B01J 2208/00893; B01J 8/0055; B01J 8/1836; B01J 8/24; B01J 8/26; B01J 8/34
See application file for complete search history.

(56) References Cited

U.S. PATENT DOCUMENTS

| | | | |
|---|---|---|---|
| 3,702,668 | A | 11/1972 | Landen |
| 3,702,886 | A | 11/1972 | Argauer et al. |
| 3,709,979 | A | 1/1973 | Chu |

(Continued)

FOREIGN PATENT DOCUMENTS

| | | | | |
|---|---|---|---|---|
| EP | | 091751 A2 | 10/1983 | |
| EP | | 0099690 A2 * | 2/1984 | ............ B01J 8/1836 |

(Continued)

OTHER PUBLICATIONS

The international Search Report and Written Opinion of PCT/US2015/053442 dated Jan. 20, 2016.
(Continued)

*Primary Examiner* — Sharon Pregler
(74) *Attorney, Agent, or Firm* — Liza Negron

(57) ABSTRACT

Apparatuses and processes for converting an oxygenate feedstock, such as methanol and/or dimethyl ether, in a fluidized bed containing a catalyst to hydrocarbons, such as gasoline boiling components, olefins and aromatics are provided herein.

9 Claims, 18 Drawing Sheets

(51) Int. Cl.
*C10G 3/00* (2006.01)
*B01J 8/00* (2006.01)

(56) References Cited

U.S. PATENT DOCUMENTS

| | | | |
|---|---|---|---|
| 3,832,449 A | 8/1974 | Rosinski et al. | |
| 3,931,349 A | 1/1976 | Kuo | |
| 3,969,426 A | 7/1976 | Owen et al. | |
| 3,998,899 A | 12/1976 | Daviduk et al. | |
| 4,016,218 A | 4/1977 | Haag et al. | |
| 4,016,245 A | 4/1977 | Plank et al. | |
| 4,025,575 A | 5/1977 | Chang et al. | |
| 4,035,430 A | 7/1977 | Dwyer et al. | |
| 4,076,842 A | 2/1978 | Plank et al. | |
| 4,079,095 A | 3/1978 | Givens et al. | |
| 4,083,889 A | 4/1978 | Caesar et al. | |
| RE29,948 E | 3/1979 | Dwyer et al. | |
| 4,234,231 A | 11/1980 | Yan | |
| 4,431,856 A * | 2/1984 | Daviduk | B01J 8/26 585/469 |
| 4,476,338 A | 10/1984 | Chang et al. | |
| 4,556,477 A | 12/1985 | Dwyer | |
| 4,582,815 A | 4/1986 | Bowes | |
| 4,677,242 A | 6/1987 | Kaiser | |
| 4,752,641 A | 6/1988 | Koyama et al. | |
| 2006/0147355 A1 | 7/2006 | Beech, Jr. et al. | |
| 2006/0149109 A1 | 7/2006 | Ruziska et al. | |

FOREIGN PATENT DOCUMENTS

| | | |
|---|---|---|
| EP | 0099690 A2 | 2/1984 |
| EP | 0216604 A1 | 4/1987 |

OTHER PUBLICATIONS

The International Search Report and Written Opinion of PCT/US2015/053447 dated Mar. 31, 2016.

* cited by examiner

APPARATUS AND PROCESS FOR PRODUCING GASOLINE, OLEFINS AND AROMATICS FROM OXYGENATES

CROSS-REFERENCE TO RELATED APPLICATIONS

This application claims the benefit of provisional U.S. Ser. Nos. 62/062,396 and 62/062,423, both filed Oct. 10, 2014, the entire contents of each of which are expressly incorporated by reference herein.

FIELD OF THE INVENTION

The present invention relates to converting an oxygenate feedstock, such as methanol and dimethyl ether, in a fluidized bed containing a catalyst to hydrocarbons, such as gasoline boiling components, olefins and aromatics.

BACKGROUND OF THE INVENTION

Processes for converting lower oxygenates such as methanol and dimethyl ether (DME) to hydrocarbons are known and have become of great interest because they offer an attractive way of producing liquid hydrocarbon fuels, especially gasoline, from sources which are not petrochemical feeds. In particular, they provide a way by which methanol and DME can be converted to gasoline boiling components, olefins and aromatics. Olefins and aromatics are valuable chemical products and can serve as feeds for the production of numerous important chemicals and polymers. Because of the limited supply of competitive petroleum feeds, the opportunities to produce low cost olefins from petroleum feeds are limited. However, methanol may be readily obtained from coal by gasification to synthesis gas and conversion of the synthesis gas to methanol by well-established industrial processes. As an alternative, the methanol may be obtained from natural gas or biomass by other conventional processes.

Available technology to convert methanol and other lower oxygenates to hydrocarbon products utilizes a fixed bed process, such as the processes described in U.S. Pat. Nos. 3,998,899; 3,931,349 and 4,035,430. In the fixed bed process, the methanol is usually first subjected to a dehydrating step, using a catalyst such as gamma-alumina, to form an equilibrium mixture of methanol, DME and water. This mixture is then passed at elevated temperature and pressure over a catalyst for conversion to the hydrocarbon products which are mainly in the range of light gas to gasoline. The fixed bed process uses a recycle gas for temperature control and very large heat transfer to manage low quality heat, which results in high compression costs and a large heat exchange network. Typically, a fixed bed process is a multi-reactor, unsteady state operation, which requires a large bore valving system to control the process.

In contrast, direct cooling of the reactor in the fluidized bed process eliminates the need for recycle gas for temperature control, which simplifies the heat exchange. Further, the fluidized bed process with continuous catalyst regeneration is a steady state operation with constant product yield. Thus, the fluidized bed process requires lower capital costs and savings on operating expenses compared to the fixed bed process. However, current fluidized bed processes typically have a low product yield. For example, $C_{5+}$ gasoline yield from a fluidized bed process ranges from 65 wt % to 75 wt % of hydrocarbons (HC), while the $C_{5+}$ gasoline yield from a fixed bed process ranges from 80 wt % to 90 wt % of HC. Thus, an alkylation unit is usually required to increase $C_{5+}$ gasoline yield in a fluidized bed process. Therefore, there is a need to provide fluidized bed processes for converting oxygenates to hydrocarbons with increased product yields and further, without the use of an alkylation unit.

SUMMARY OF THE INVENTION

It has been found that hydrocarbon product yields can be increased without the need for an alkylation unit by providing apparatuses and processes for converting oxygenates in a fluidized reactor bed by staging the reactor, operating the reactor at a higher pressure and lower temperature, and/or providing a recycle stream, such as light olefins.

Thus, in one aspect, embodiments of the invention provide a process for converting an oxygenate feedstock to a $C_{5+}$ gasoline product comprising: feeding the oxygenate feedstock to a fluidized bed reactor under conditions to convert the oxygenate feedstock to a hydrocarbon mixture in a reactor effluent, wherein the fluid bed reactor comprises: (i) a catalyst; and (ii) at least one packing layer; cooling the reactor effluent comprising the hydrocarbon mixture and condensing a portion of the reactor effluent to form a mixed phase effluent; separating the mixed phase effluent into an aqueous liquid phase, a hydrocarbon gas phase and a hydrocarbon liquid phase; separating a $C_{4-}$ light gas comprising $C_2$-$C_4$ olefins and the $C_{5+}$ gasoline product from the hydrocarbon gas phase and the hydrocarbon liquid phase.

In another aspect, embodiments of the invention provide an apparatus for producing a $C_{5+}$ gasoline product comprising: a fluidized bed reactor comprising: (i) a fluid inlet for a feedstock; (ii) a catalyst; and (iii) at least one packing layer; a cooler for cooling the reactor effluent and condensing a portion of the reactor effluent to form a mixed phase effluent; a separator for separating the mixed phase effluent into a gas hydrocarbon stream, a water stream, and a liquid hydrocarbon stream; a means for transporting the reactor effluent from the fluid bed reactor to the separator; at least one fractionating column for producing the $C_{5+}$ gasoline product; and a means for transporting the liquid hydrocarbon stream and gas hydrocarbon stream to the at least one fractionating column.

In still another aspect, embodiments of the invention provide a process for converting an oxygenate feedstock to olefins comprising: feeding the oxygenate feedstock to a fluidized bed reactor under conditions to convert the oxygenate feedstock to a hydrocarbon mixture in a reactor effluent, wherein the fluid bed reactor comprises: (i) a catalyst; and (ii) at least one packing layer; cooling the reactor effluent comprising the hydrocarbon mixture and condensing a portion of the reactor effluent to form a mixed phase effluent; separating the mixed phase effluent into an aqueous liquid phase, a hydrocarbon gas phase and a hydrocarbon liquid phase; separating olefins from the hydrocarbon gas phase and the hydrocarbon liquid phase.

In still another aspect, embodiments of the invention provide a process for converting an oxygenate feedstock to aromatics comprising: feeding the oxygenate feedstock to a fluidized bed reactor under conditions to convert the oxygenate feedstock to a hydrocarbon mixture in a reactor effluent, wherein the fluid bed reactor comprises: (i) a catalyst; and (ii) at least one packing layer; cooling the reactor effluent comprising the hydrocarbon mixture and condensing a portion of the reactor effluent to form a mixed phase effluent; separating the mixed phase effluent into an aqueous liquid phase, a hydrocarbon gas phase and a hydrocarbon liquid phase; separating aromatics from the hydrocarbon gas phase and the hydrocarbon liquid phase.

Other embodiments, including particular aspects of the embodiments summarized above, will be evident from the detailed description that follows.

DETAILED DESCRIPTION OF THE INVENTION

Figure 1:
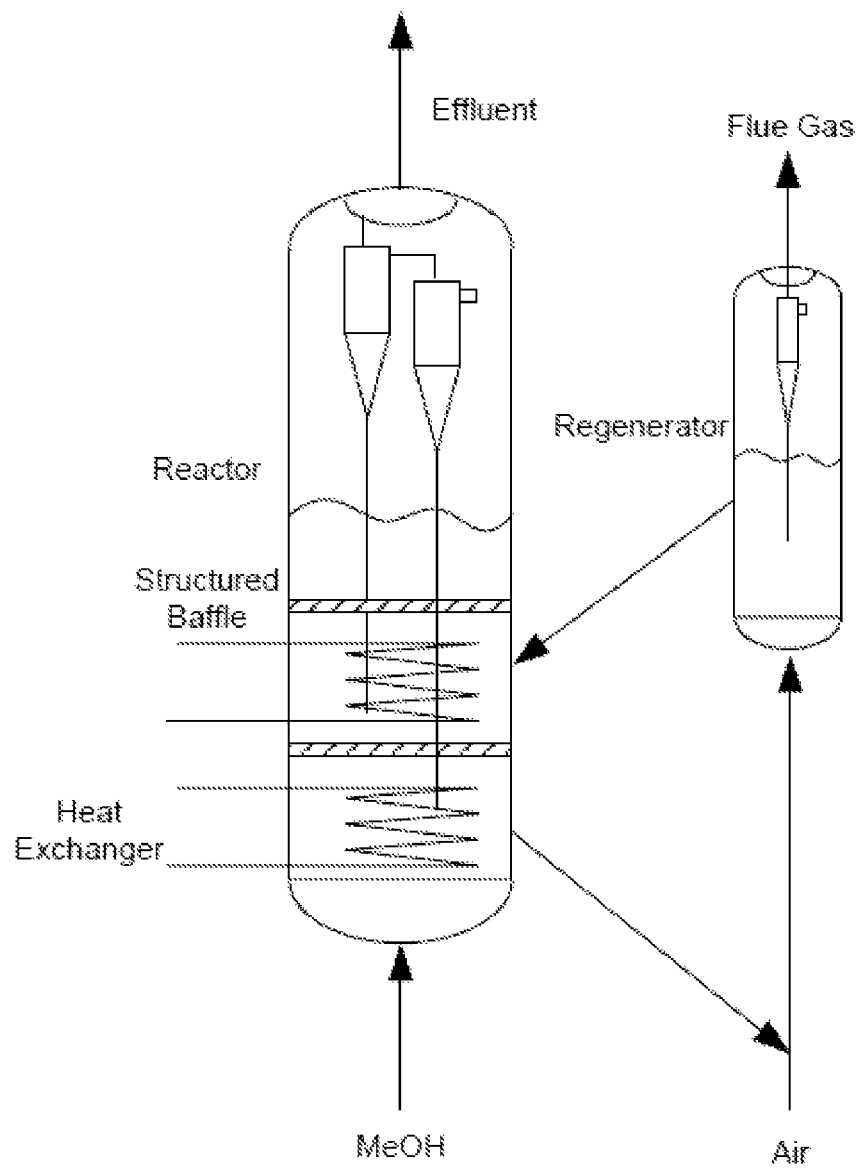
FIG. 1 illustrates a staged fluidized bed reactor with internal cooling useful for methanol to aromatics (MTA) and/or methanol to olefins (MTO) processes.
Figure 2:
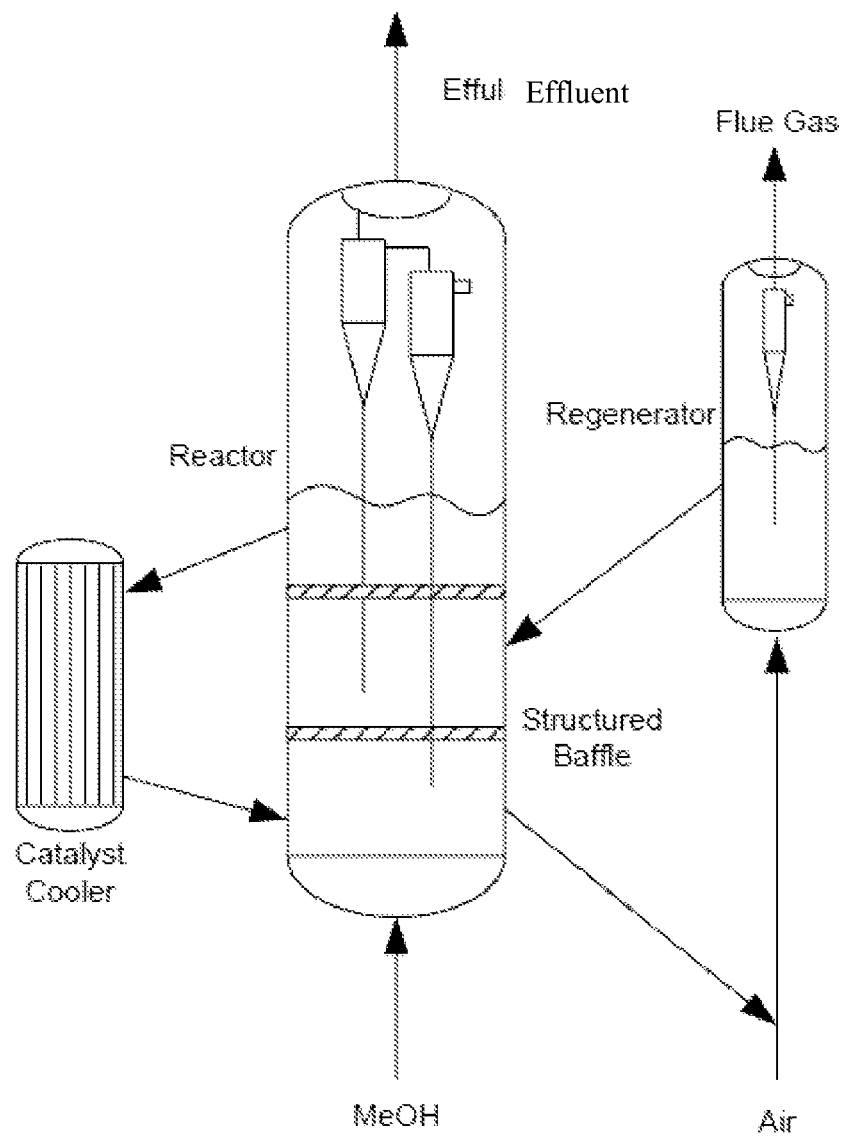
FIG. 2 illustrates a staged fluidized bed MTA/MTO reactor with external cooling.

In various aspects of the invention, apparatuses and processes for converting oxygenates, such as methanol and DME, in a fluidized bed comprising a catalyst to hydrocarbons, such as gasoline, olefins and aromatics are provided.

I. Definitions

As used herein, the term "aromatic" refers to unsaturated cyclic hydrocarbons have 6 to 18 ring carbon atoms (e.g., 6 to 12 ring carbon atoms), such as but not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, the term "olefin" refers to an unsaturated hydrocarbon chain of 2 to about 12 carbon atoms in length containing at least one carbon-to-carbon double bond. The olefin may be straight-chain or branched-chain. Non-limiting examples include ethylene, propylene, butylene, and pentenyl. "Olefin" is intended to embrace all structural isomeric forms of olefins. As used herein, the term "light olefin" refers to olefins having 2 to 4 carbon atoms (i.e., ethylene, propylene, and butenes).

As used herein, the term "paraffin" refers to a saturated hydrocarbon chain of 1 to about 12 carbon atoms in length, such as, but not limited to methane, ethane, propane and butane. The paraffin may be straight-chain or branched-chain. "Paraffin" is intended to embrace all structural isomeric forms of paraffins. As used herein, the term "light paraffin" refers to paraffins having 1 to 4 carbon atoms (i.e., methane, ethane, propane and butane).

As used herein, the term "oxygenate" refers to oxygen-containing compounds having 1 to about 20 carbon atoms, 1 to about 10 carbon atoms, or 1 to about 4 carbon atoms. Exemplary oxygenates include alcohols, ethers, carbonyl compounds, e.g., aldehydes, ketones and carboxylic acids, and mixtures thereof. Particular non-limiting examples of oxygenates include methanol, ethanol, dimethyl ether, diethyl ether, methylethyl ether, di-isopropyl ether, dimethyl carbonate, dimethyl ketone, formaldehyde, acetic acid, and the like, and combinations thereof.

As used herein, the term "$C_{5+}$ gasoline" refers to a composition comprising $C_5$-$C_{12}$ hydrocarbons and/or having a boiling point range within the specifications for motor gasoline (e.g., from about 100° F. to about 400° F.).

As used herein, the term "coke" refers to a carbonaceous solid or liquid material resulting from conversion of an oxygenate to a hydrocarbon.

As used herein, the term "liquefied petroleum gas" or "LPG" refers to a mixture of hydrocarbons in a liquid state, in particular propane and butane.

II. Converting an Oxygenate to a Hydrocarbon Product

In a first embodiment, an oxygenate feedstock can be fed into a fluidized bed reactor comprising a catalyst, and the oxygenate can be converted into a hydrocarbon product, which can be further separated into various hydrocarbon components. The hydrocarbon product yield can be improved by staging the fluidized bed reactor, by operating the reactor at a relatively high pressure and/or at a relatively low temperature, and/or by providing a gas recycle stream to the reactor.

In various aspects, the oxygenated hydrocarbon feedstock can comprise methanol, DME, or a mixture thereof. The methanol can be obtained from coal, natural gas and biomass by conventional processes.

In various aspects, the hydrocarbon product can comprise $C_{5+}$ gasoline, aromatics, and/or olefins.

In one aspect, the gas recycle stream can comprise olefins.

III. Structured Packing

In any embodiment, the fluidized bed reactor can include at least one layer of structured packing as a staging baffle. A deep fluidized bed design can be used for the reactor due to the weight hourly space velocity (WHSV) required by the chemical reactions. However, a deep fluidized bed can be prone to gas back-mixing and gas by-pass. Therefore, it can be important to minimize gas back-mixing and gas by-pass to maintain oxygenate conversion and maximize product yield. The gas back-mixing and gas by-pass can be minimized by installing at least one layer of structured packing which functions as a staging baffle in the fluidized bed reactor. Advantageously, the fluidized bed reactor can include at least two layers of structured packing FIGS. 1, 2, 12, and 13 show a fluid bed reactor with two layers of structured packing as two structured baffles. However, in various aspects, the fluidized bed reactor can include from one to eight layers of structured packing.

An example of the structured packing is a one foot thick layer of Koch-Glitsch KFBE IIB, which separates the dense fluid bed into multiple stages. Structured packing is commonly used in distillation towers in separation processes. This type of packing can be useful because of its high open area for both gas and catalyst solids to pass through and its capability to control bubble sizes. When larger bubbles from a lower stage reach the staging baffles, gas can be redistributed by the structured packing and form smaller bubbles into the next higher stage.

IV. Production of Gasoline

In a methanol to gasoline (MTG) process, methanol can first be dehydrated to form dimethyl ether. The methanol and/or dimethyl ether can then be converted in a series of reactions that result in formation of a hydrocarbon mixture that can comprise aromatics, paraffins, and olefins, among other types of hydrocarbon products. This mixture may be separated into a LPG fraction and a high-quality gasoline fraction, e.g., comprising aromatics, paraffins, and olefins.

In one embodiment, the oxygenate feedstock comprises methanol, which is fed into a fluidized bed reactor and converted to gasoline boiling components in an MTG process. In some embodiments, the methanol can be obtained from coal with a water content up to about 15%, for example from about 5% to about 10%, and/or from natural gas with a water content up to about 40%, for example from about 30% to about 40%.

Traditionally, $C_{5+}$ gasoline yield in MTG processes can be in the range of 65-72 wt %, based on the feed, when relatively high temperatures (~715-800° F.) and/or relatively low pressures (~25-45 psig) are used in the MTG reactor. However, it is believed that the $C_{5+}$ gasoline yield of the fluid bed MTG process can be improved to at least about 80 wt %, for example about 80 to about 90 wt %, about 80 to about 85 wt %, about 85 to about 90 wt %, or about 86 to about 95 wt %, as compared to the feed, advantageously without the need for an alkylation unit by staging the reactor, by operating the reactor at a higher pressure and lower temperature, and/or by recycling the light olefins. The spent catalysts from the reactor can be transferred to the regenerator to regenerate the catalyst by burning the coke off. The regenerated catalysts can then be transferred back to the reactor.

Alternatively or additionally, the oxygenate feedstock can comprise DME, which can be fed into a fluidized bed reactor and converted to gasoline boiling components. The DME to gasoline process can achieve a $C_{5+}$ gasoline yield of greater than 70 wt %, for example at least about 75 wt %, at least about 80 wt %, about 75 to about 95 wt %, about 75 to about 90 wt %, about 80 to about 90 wt %, about 80 to about 85 wt %, about 85 to about 90 wt %, or about 86 to about 95 wt %, as compared to the feed, advantageously without the need for an alkylation unit by staging the reactor, by operating the reactor at a higher pressure and lower temperature, and/or by recycling the light olefins. The spent catalysts from the reactor can be transferred to the regenerator to regenerate the catalyst by burning the coke off. The regenerated catalysts can then be transferred back to the reactor.

In any embodiment, the fluidized bed reactor can include at least one layer of structured packing as a staging baffle. In various aspects, the fluid bed reactor can include from one to eight layers of structured packing. Advantageously, the fluid bed reactor can include at least two layers of structured packing. By including structured packing, it is believed that the $C_{5+}$ gasoline yield can be further improved by at least 2-4 wt % for the MTG process.

A. Cooling the Reactor

The conversion of methanol and/or DME to gasoline boiling components is a highly exothermic reaction. For example, the MTG process releases approximately 750 BTU of heat per pound of methanol. Thus, it can often be necessary to cool the fluidized bed reactor.

In one embodiment, the fluidized bed reactor can be internally cooled, such as shown in FIGS. 1, 3, 5, 8, 10, 12, 14, and 16. For example, a heat exchanger can be present in one or more stages. FIGS. 1, 3, 5, 8, 10, 12, 14, and 16 show heat exchangers in each stage. The internal heat exchangers can function not only to remove the heat from the reactor but also as internal baffles, operating to break up large bubbles and thus reduce gas by-pass. With internal heat exchangers, controlling the temperature at each stage is also achievable, which can provide the ability to adjust the process operation to improve (maximize) desired product (e.g., $C_{5+}$ gasoline) yield.

Additionally or alternatively, the fluidized bed reactor can be externally cooled, as shown in FIGS. 2, 4, 6, 7, 9, 11, 13, 15, 17, and 18. For example, a catalyst cooler can be installed for removing the heat from the reactor by circulating the catalyst between the reactor and the cooler, as shown in FIGS. 2, 4, 6, 7, 9, 11, 13, 15, 17, and 18.

With in-bed heat exchangers and/or external catalyst cooler(s), a relatively uniform temperature distribution within the operating range can be achieved in the fluidized bed process. While the internal cooling option can be easier to operate, the external cooling option can provide more flexibility for operation and a less complicated construction, especially for a large scale unit.

B. Operating Conditions

The fluidized bed reactor can be operated at pressure from about 25 psig to about 400 psig, for example from about 75 psig to about 400 psig, from about 75 psig to about 300 psig, from about 75 psig to about 200 psig, from about 100 psig to about 400 psig, from about 100 psig to about 300 psig, from about 100 psig to about 200 psig, from about 150 psig to about 350 psig, at about 150 psig, at about 200 psig, or at about 250 psig. The fluidized bed reactor can be operated at a temperature from about 500° F. to about 900° F., for example from about 550° F. to about 900° F., from about 600° F. to about 900° F., from about 700° F. to about 900° F., from about 500° F. to about 750° F., from about 500° F. to about 700° F., from about 500° F. to about 650° F., from about 600° F. to about 700° F., from about 550° F. to about 700° F., from about 550° F. to about 650° F., from about 550° F. to about 600° F., at about 550° F., at about 600° F., at about 650° F., or at about 700° F. Further, the methanol WHSV can be from about 0.2 kg/kg-hr to about 3.0 kg/kg-hr, for example from about 0.5 kg/kg-hr to about 2.5 kg/kg-hr, from about 1 kg/kg-hr to about 2.0 kg/kg-hr, at about 1.7 kg/kg-hr, or at about 1.5 kg/kg-hr, during operation. Under these operating conditions, it is believed that the desired product (e.g., $C_{5+}$ gasoline) yield can be improved by at least 4-6 wt % (for the MTG process).

C. Catalysts

The conversion reactions described herein typically utilize a catalyst. Useful catalyst compositions for MTG processes can comprise bound zeolite catalysts and unbound zeolite catalysts.

Generally, the zeolite employed in the present catalyst composition can typically have a silica to alumina molar ratio of at least 40, e.g., from about 40 to about 200. Additionally or alternately, the zeolite can comprise at least one medium pore aluminosilicate zeolite having a Constraint Index of 1-12 (as defined in U.S. Pat. No. 4,016,218). Suitable zeolites can include, but are not necessarily limited to, ZSM-5, ZSM-11, ZSM-12, ZSM-22, ZSM-23, ZSM-35, ZSM-48, and the like, as well as combinations thereof. ZSM-5 is described in detail in U.S. Pat. No. 3,702,886 and RE 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. In certain embodiments, the zeolite can comprise, consist essentially of, or be ZSM-5. The ZSM-5 can have a silica to alumina ratio of 55:1.

When used in the present catalyst composition, the zeolite can advantageously be present at least partly in the hydrogen form. Depending on the conditions used to synthesize the zeolite, this may implicate converting the zeolite from, for example, the alkali (e.g., sodium) form. This can readily be achieved, e.g., by ion exchange to convert the zeolite to the ammonium form, followed by calcination in air or an inert atmosphere at a temperature from about 400° C. to about 700° C. to convert the ammonium form to the active hydrogen form. If an organic structure directing agent is used in the synthesis of the zeolite, additional calcination may be desirable to remove the organic structure directing agent.

The catalysts described herein can be pretreated with steam prior to use in the reactor.

To enhance the steam stability of the zeolite without excessive loss of its initial acid activity, the present catalyst composition can contain phosphorus in an amount between about 0.01 wt % and about 3 wt % elemental phosphorus, e.g., between about 0.05 wt % and about 2 wt %, of the total catalyst composition. The phosphorus can be added to the catalyst composition at any stage during synthesis of the zeolite and/or formulation of the zeolite and binder into the catalyst composition. Generally, phosphorus addition can be achieved by spraying and/or impregnating the final catalyst composition (and/or a precursor thereto) with a solution of a phosphorus compound. Suitable phosphorus compounds can include, but are not limited to, phosphinic [$H_2PO(OH)$], phosphonic [$HPO(OH)_2$], phosphinous, phosphorus, and phosphoric [$PO(OH)_3$] acids, salts and esters of such acids, phosphorus halides, and the like, and combinations thereof. After phosphorus treatment, the catalyst can generally be calcined, e.g., in air at a temperature from about 400° C. to about 700° C. to convert the phosphorus to an oxide form.

In one embodiment, the catalyst is modified with up to 3 wt % phosphorous for improved stability.

Additionally or alternatively, the catalyst composition can include up to 80% clay by weight, for example up to 50 wt % clay, up to 40 wt % clay, or up to 30 wt % clay.

D. Recycling Light Olefins

In some embodiments, the desired product (e.g., $C_{5+}$ gasoline) yield can be improved by recycling $C_{4-}$ light gas (e.g., which light gas can comprise olefins to convert ethylene, propylene, and butenes to $C_{5+}$ gasoline). For a fixed bed MTG process, the $C_{5+}$ gasoline yield can be in the range of about 80-90 wt % with a light gas recycle ratio of about 6-9. For a fluid bed MTG process, by recycling the $C_{4-}$ light gas with a recycle ratio of up to 3, it is believed that the $C_{5+}$ gasoline yield can be further improved by at least about 8-12 wt %. Additionally or alternately, recycling light gas can improve the stabilization of the fluidized bed reactor hydrodynamics. The olefins can be recycled to the main reactor (FIGS. 3-4 and 14-15) or to a second reactor (FIGS. 5-7 and 16-18).

Table 1 can represent a product yield for a fluid bed MTG process. As shown in Table 1, $C_{5+}$ gasoline yield is about 67 wt %, and light olefin yield (including ethylene, propylene, and butenes) is about 17 wt %. By recycling the light olefins and converting all of them to $C_{5+}$ gasoline, the potential $C_{5+}$ gasoline yield can be about 84 wt %, which can then compare more favorably to fixed bed MTG gasoline yields. Considering the steady state operation, uniform temperature distribution in the reactor with direct cooling and smaller recycle heater and compressor, the fluid bed MTG process can provide both the capital and operating cost advantages over the fixed bed MTG process.

TABLE 1

Typical Product Yield of a Fluid Bed MTG Process
Fluid Bed MTG Yield
Hydrocarbon Product. wt % of HC

| | |
|---|---|
| Light Gas | 2.7 |
| Ethylene | 5.4 |
| Propane | 3.5 |
| Propylene | 5.4 |
| i-Butane | 8.5 |
| n-Butane | 1.5 |
| Butenes | 5.8 |
| C5+ Gasoline | 67.2 |
| Potential C5+ Gasoline w Alkylate | 91.2 |
| Potential C5+ Gasoline w/o Alkylate | 83.8 |

Figure 3:
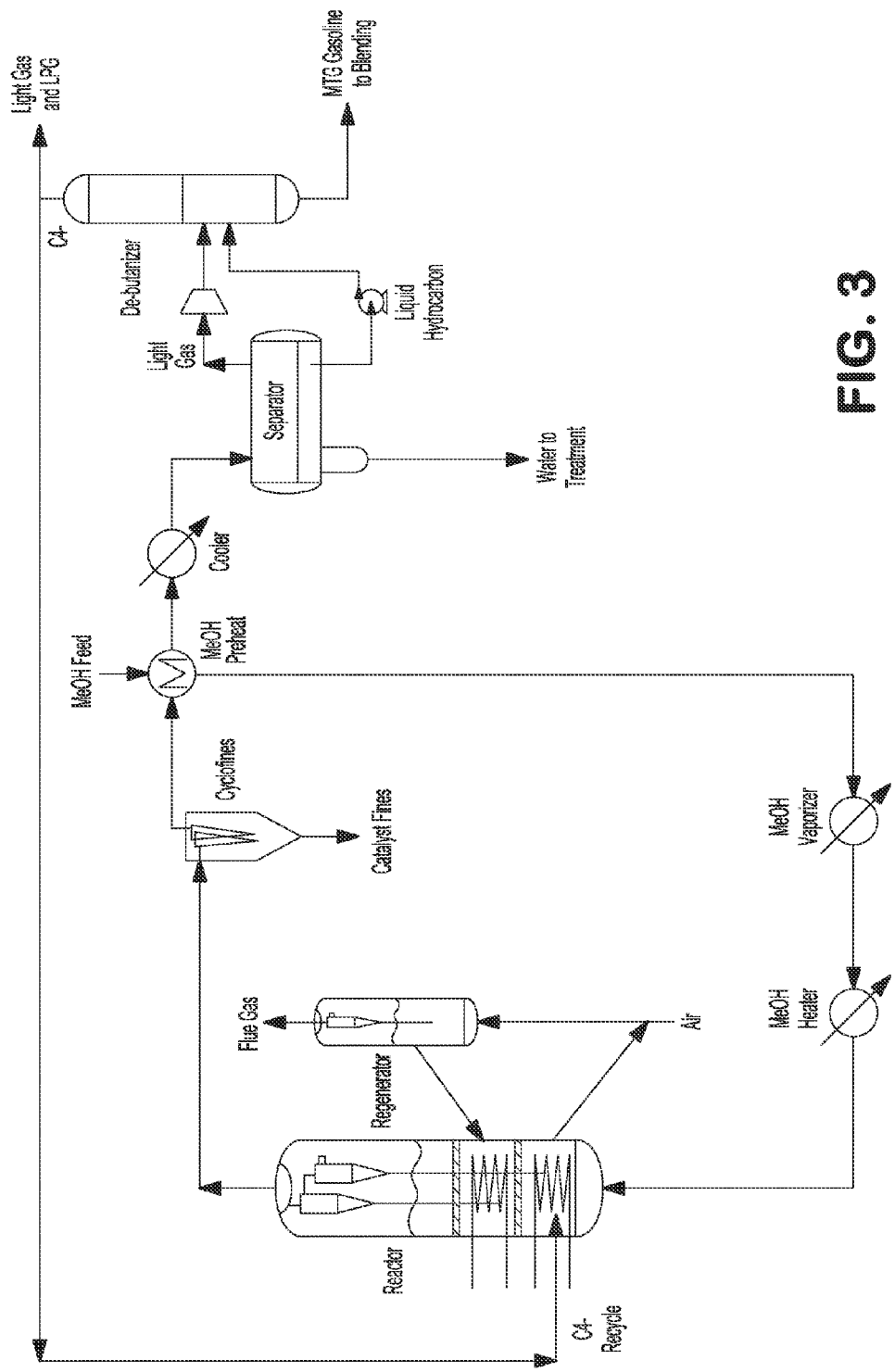
FIG. 3 illustrates an internally cooled fluidized bed MTA/MTO process with light gas recycling.
Figure 4:
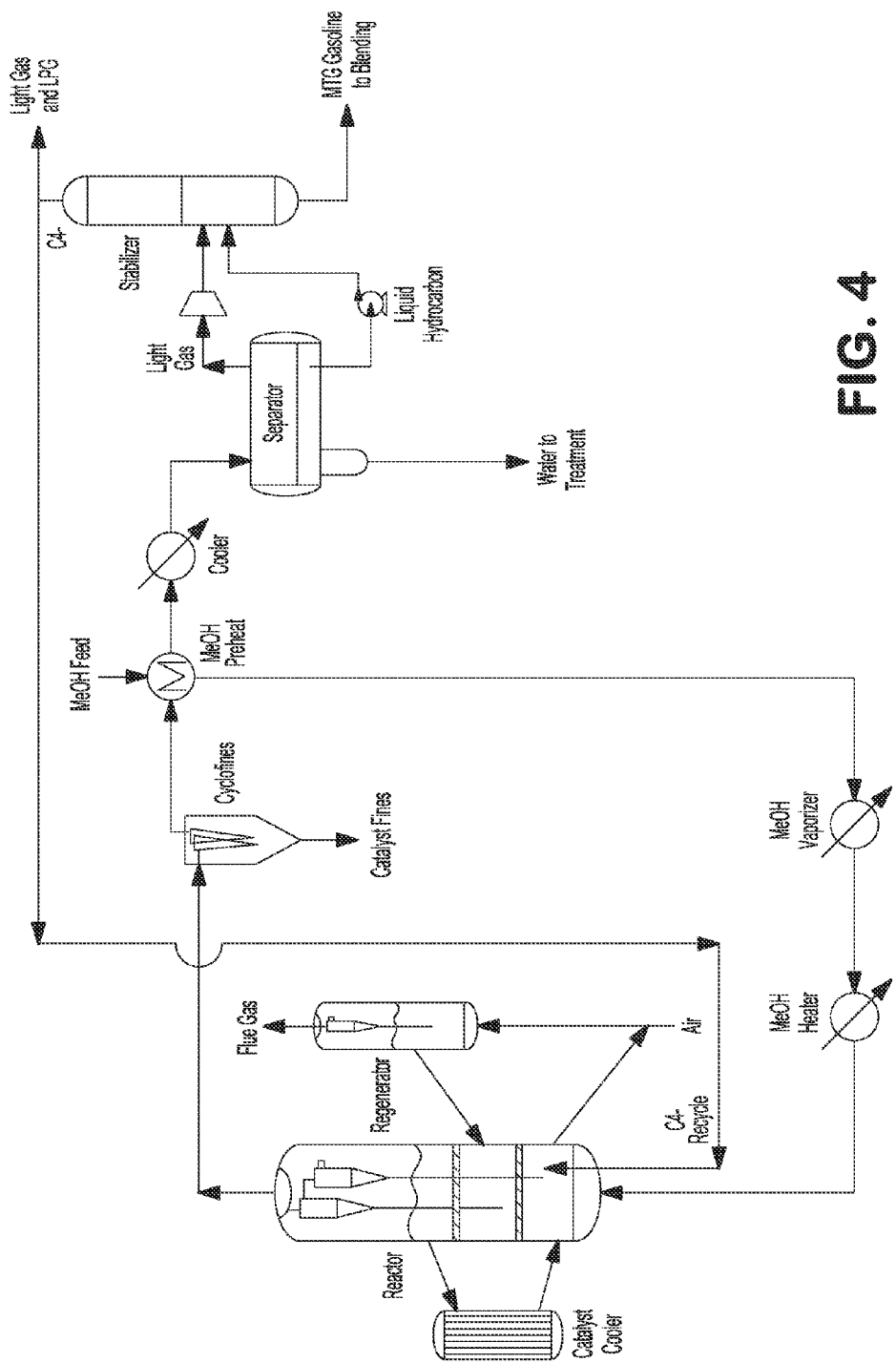
FIG. 4 illustrates an externally cooled fluidized bed MTA/MTO process with light gas recycling.
Figure 14:
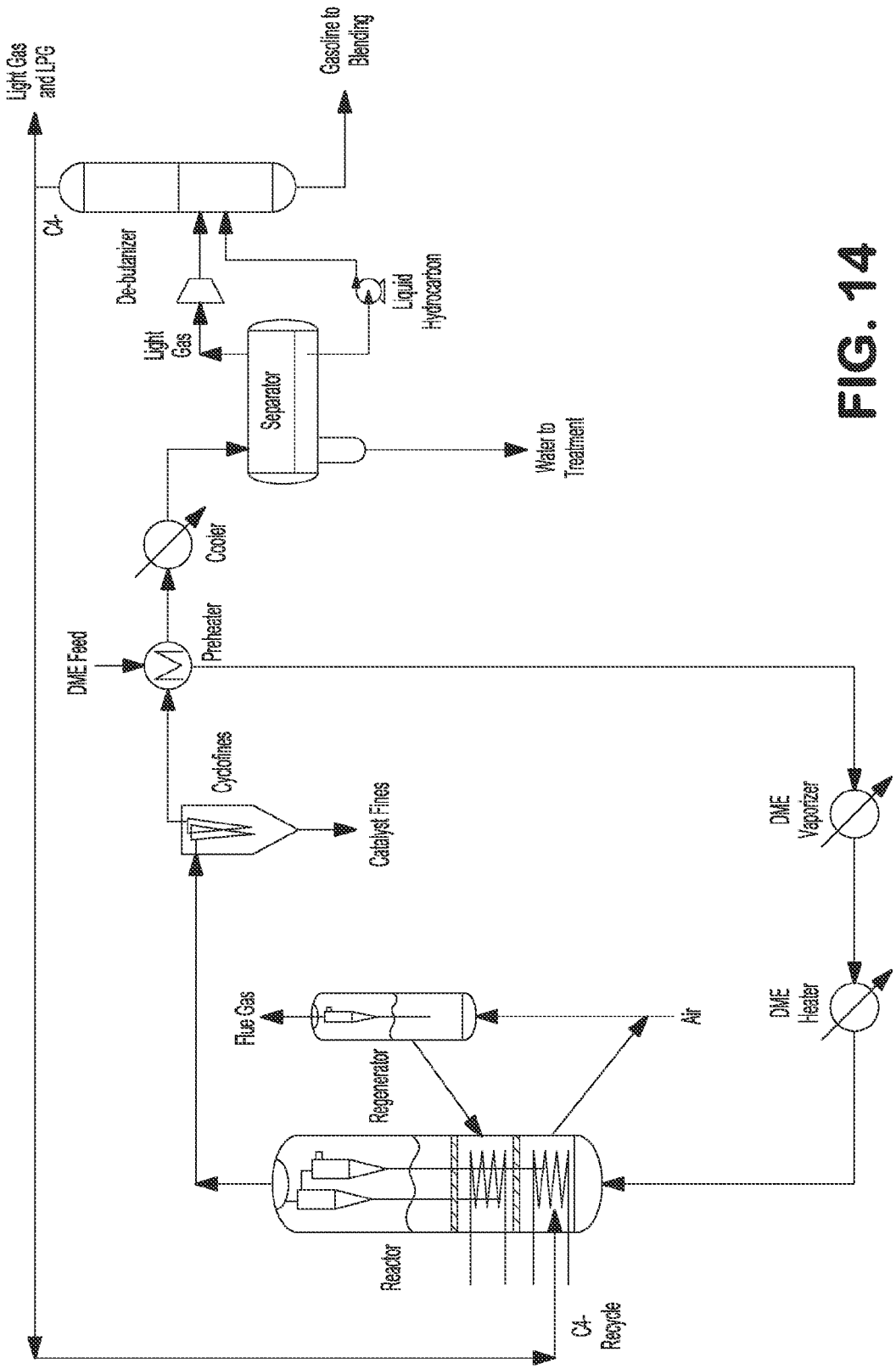
FIG. 14 illustrates an internally cooled fluidized bed process with light gas recycling with DME feedstock.
Figure 15:
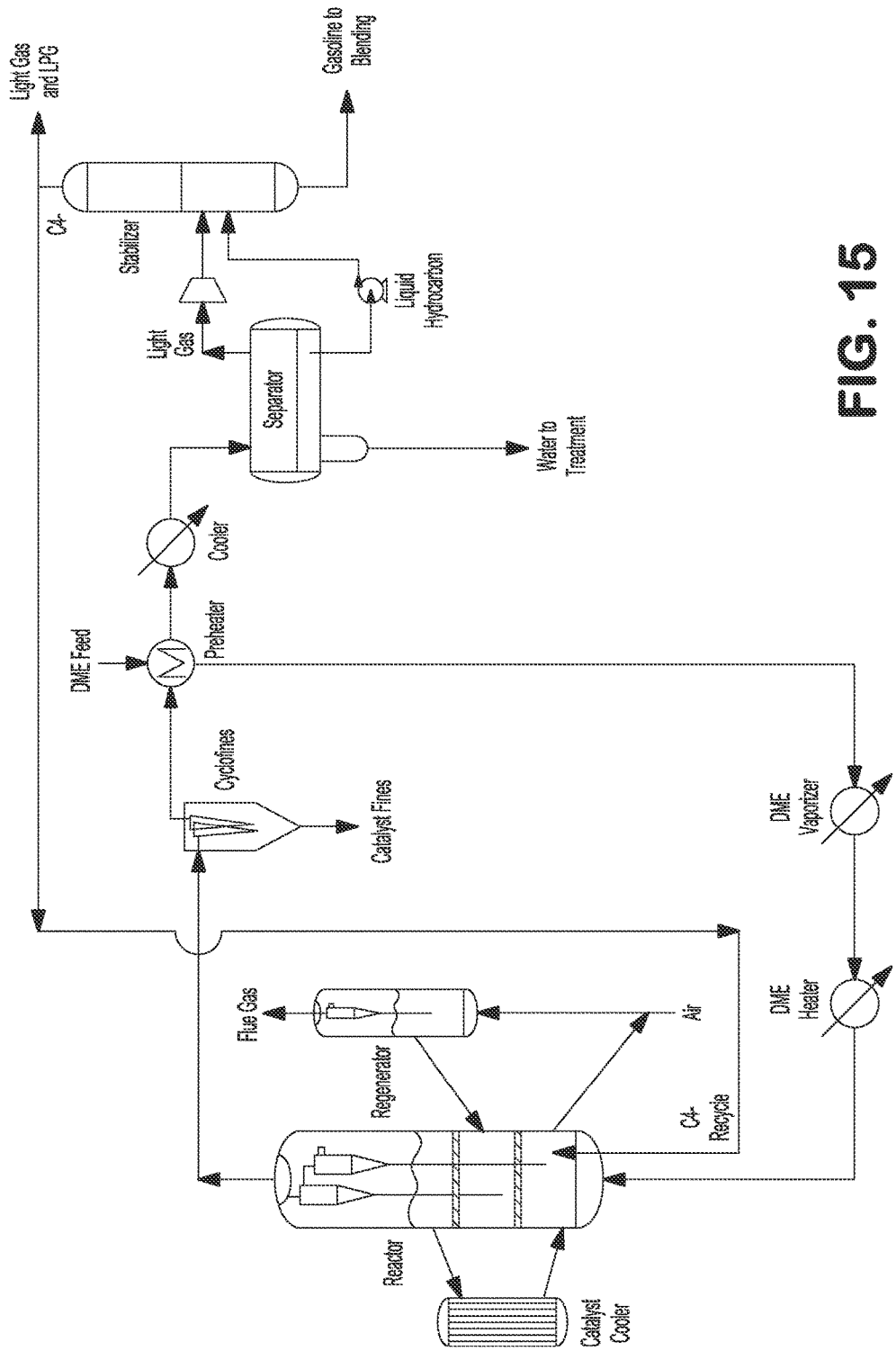
FIG. 15 illustrates an externally cooled fluidized bed process with light gas recycling with DME feedstock.

In one embodiment, $C_{4-}$ light gas comprising olefins can be recycled to the main reactor to convert ethylene, propylene, and butenes to $C_{5+}$ gasoline, as shown in FIGS. 3 and 4. Heated methanol feed can be fed to the bottom of the reactor. Reactor vapor can be separated from catalyst by a set of two stage cyclones. Reactor effluent can be sent to fines collection equipment, e.g., KBR CycloFines™, to remove catalyst fines. The reactor effluent can be further cooled and partially condensed against incoming methanol feed, and then the mixed phase effluent can be sent to a water separator where the condensed aqueous phase can be separated and sent to wastewater treatment. Separator vapor and hydrocarbon liquid can be sent to a stabilizer, where $C_{4-}$ light gas can be separated from $C_{5+}$ product. The $C_{4-}$ light gas can be recycled back to the reactor where the light olefins can be converted to $C_{5+}$ gasoline. The $C_{5+}$ gasoline product can be used immediately or sent to storage for later use. The spent catalysts from the reactor can be transferred to a regenerator to regenerate the catalyst, e.g., by burning the coke off. The regenerated catalysts can then be transferred back to the reactor. In the alternative, a DME feed can be fed to the reactor instead of or in addition to methanol feed, as shown in FIGS. 14 and 15.

Figure 10:
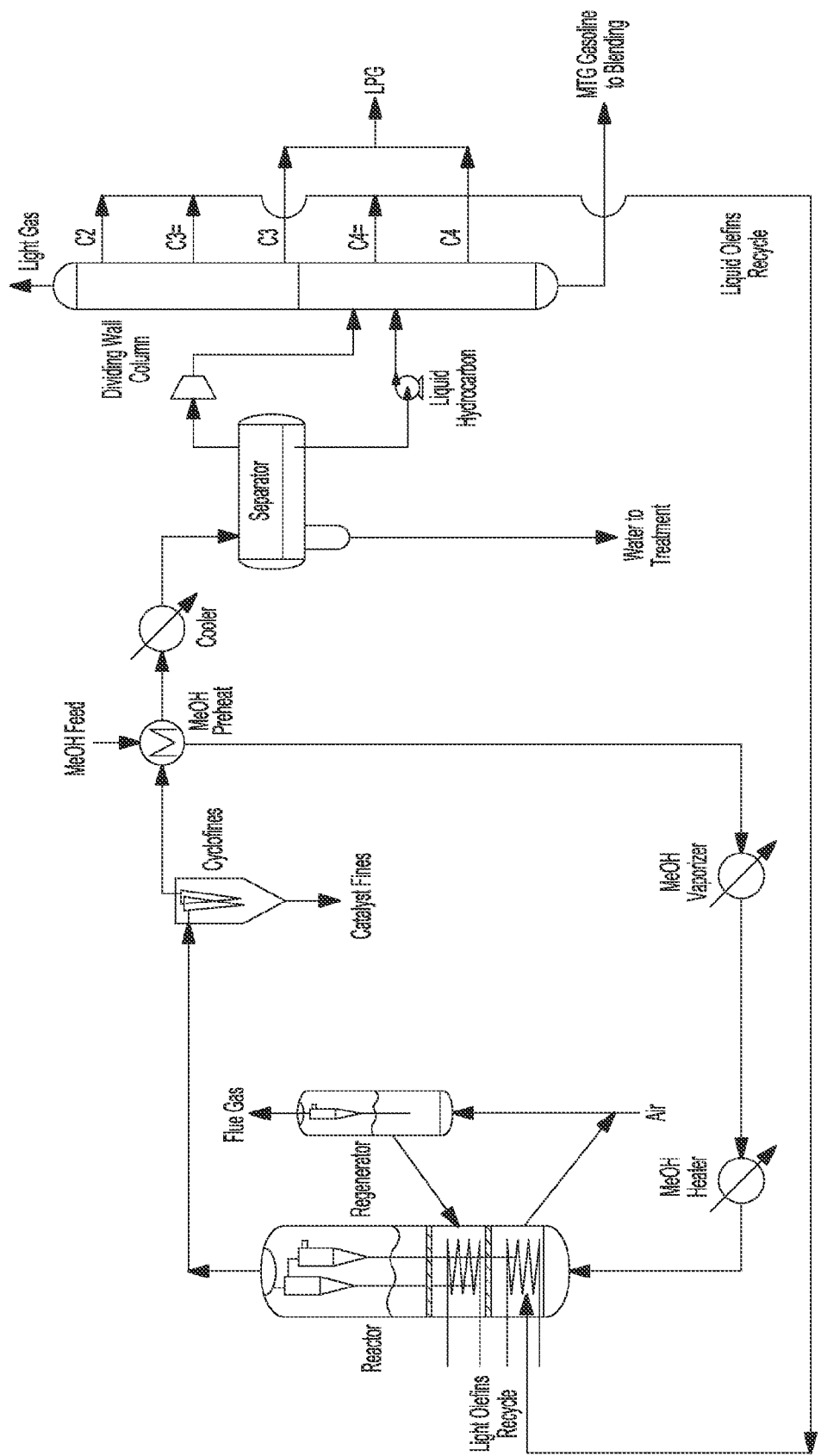
FIG. 10 illustrates an internally cooled fluidized bed MTA/MTO process with light olefins recycling.
Figure 11:
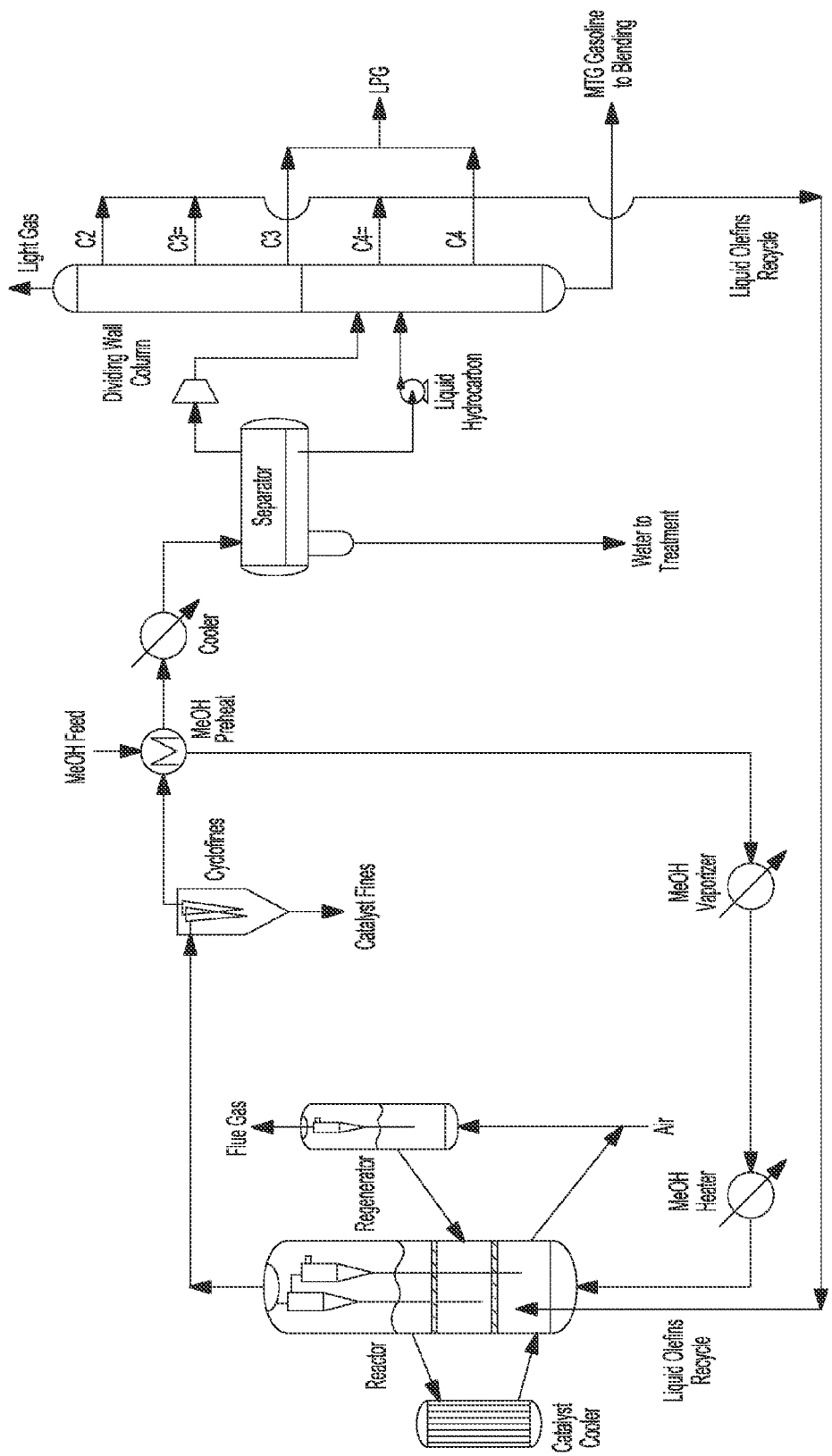
FIG. 11 illustrates an externally cooled fluidized bed MTA/MTO process with light olefins recycling.
Figure 12:
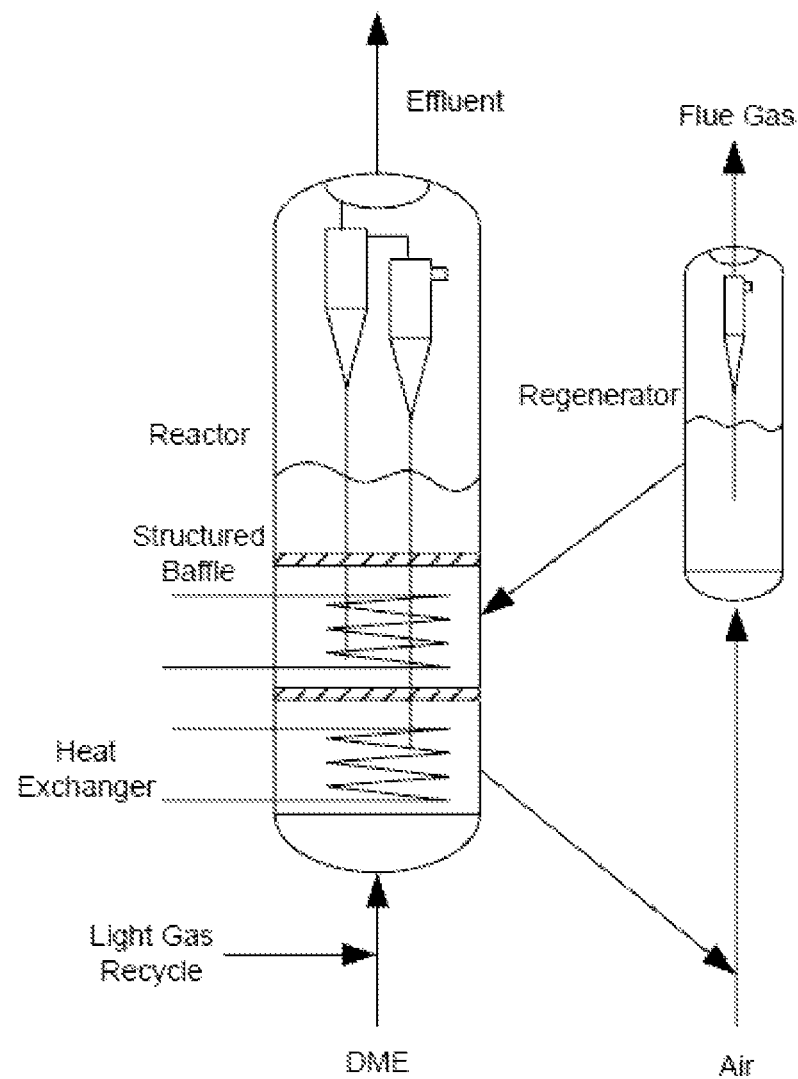
FIG. 12 illustrates a staged fluidized bed reactor with internal cooling with DME feedstock.
Figure 13:
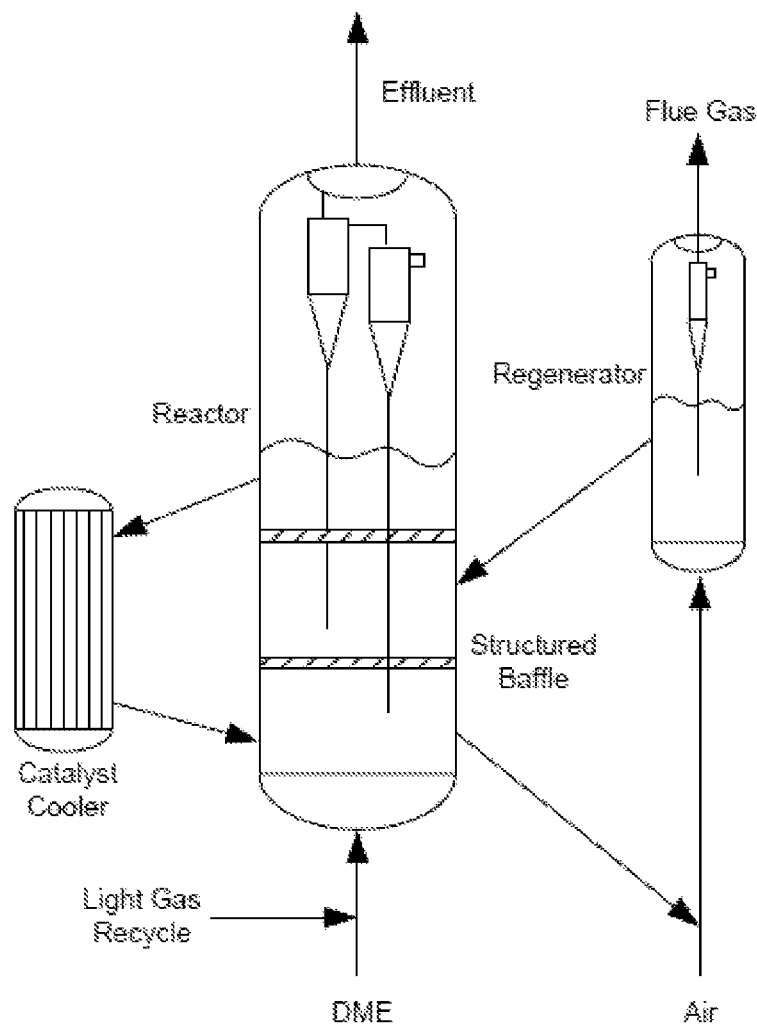
FIG. 13 illustrates a staged fluidized bed reactor with external cooling with DME feedstock.

Additionally or alternatively, after the mixed phase effluent is sent to the water separator where the condensed aqueous phase can be separated and sent to wastewater treatment, the separator vapor and hydrocarbon liquid can be sent to one or multiple dividing wall columns where multiple (e.g., seven) streams (e.g., including light gas, $C_2$, propylene, propane, butenes, butanes, and $C_{5+}$ product) can be divided, as shown in FIG. 10. In MTG processes, $C_2$, propylene, and butenes can be combined and advantageously recycled back to the reactor to be further converted to $C_{5+}$ gasoline. Propane and butanes can be combined as LPG. $C_{5+}$ gasoline product can be used immediately or sent to storage for later use.

Figure 5:
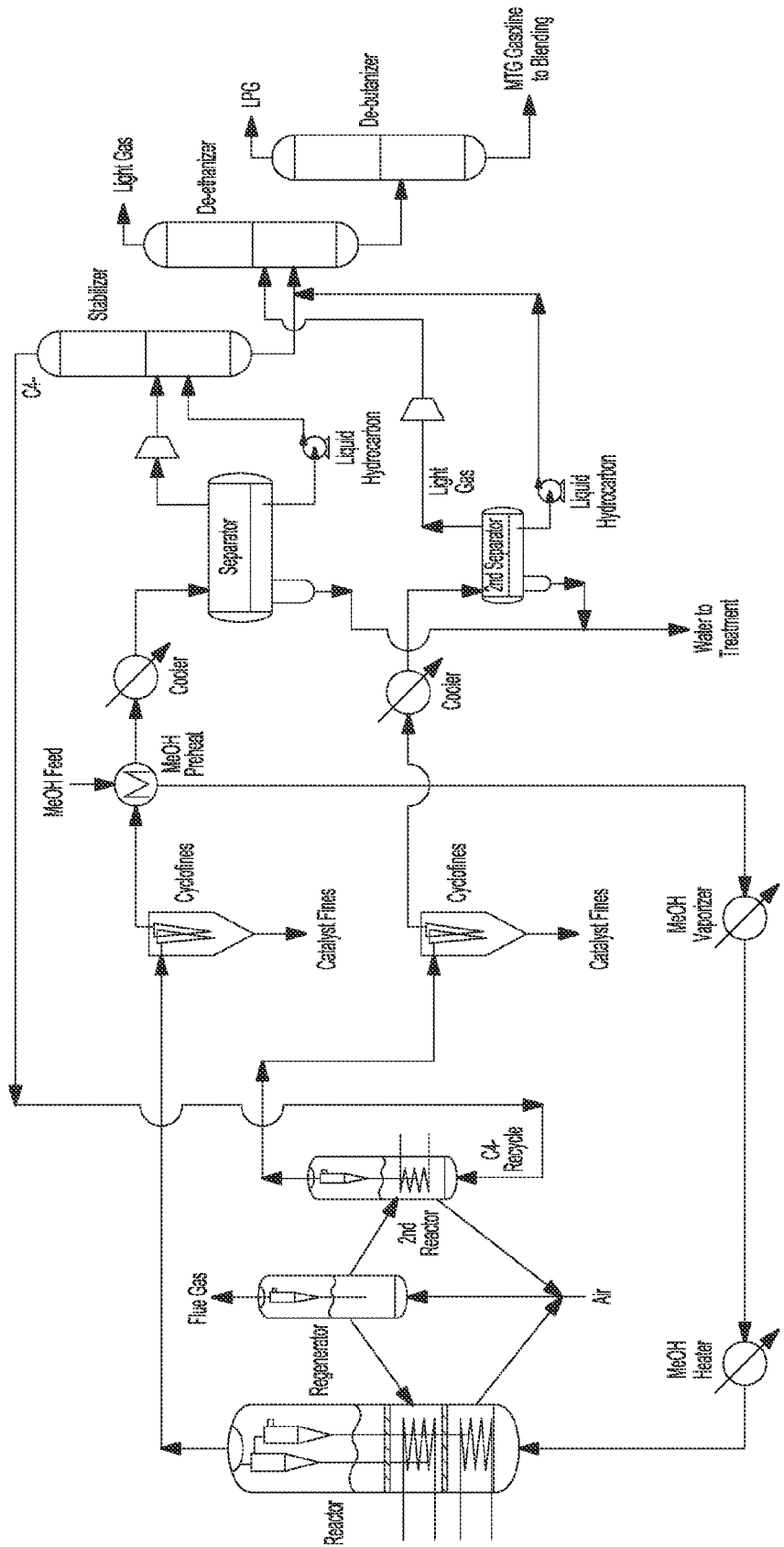
FIG. 5 illustrates an internally cooled fluidized bed MTA/MTO process with light gas recycling to a second reactor.
Figure 6:
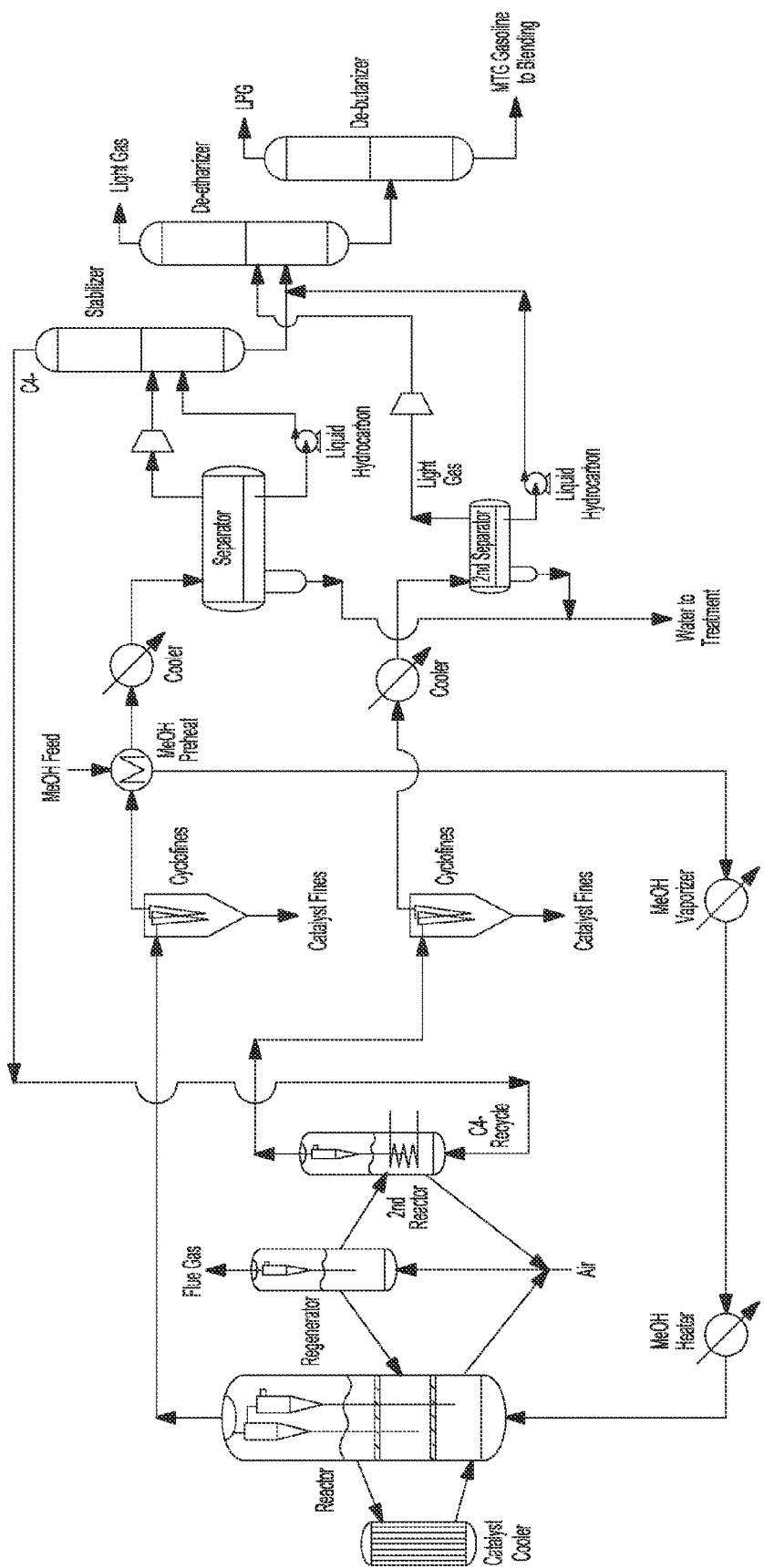
FIG. 6 illustrates an externally cooled fluidized bed MTA/MTO process with light gas recycling to a second reactor.
Figure 16:
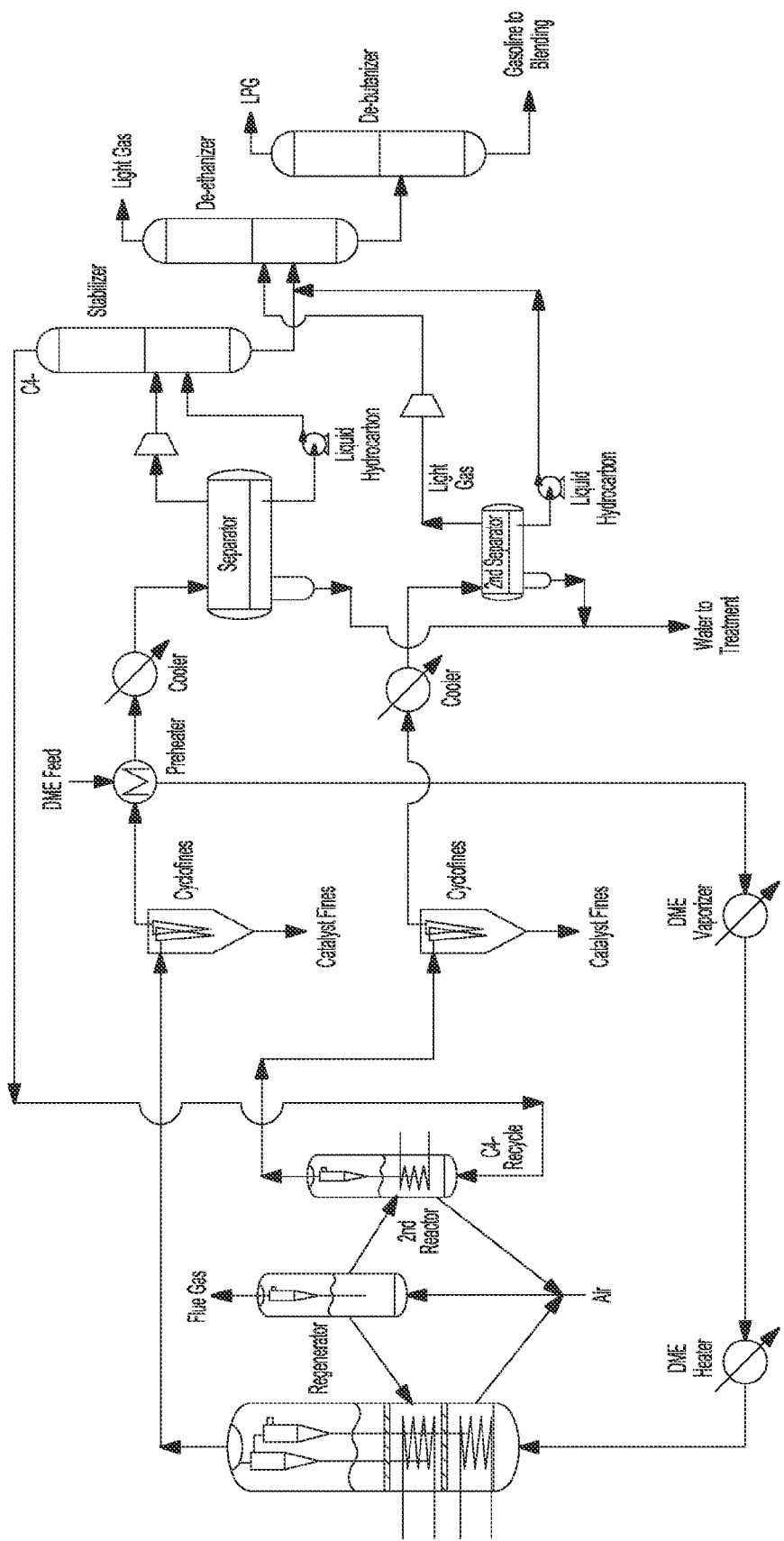
FIG. 16 illustrates an internally cooled fluidized bed process with light gas recycling to a second reactor with DME feedstock.
Figure 17:
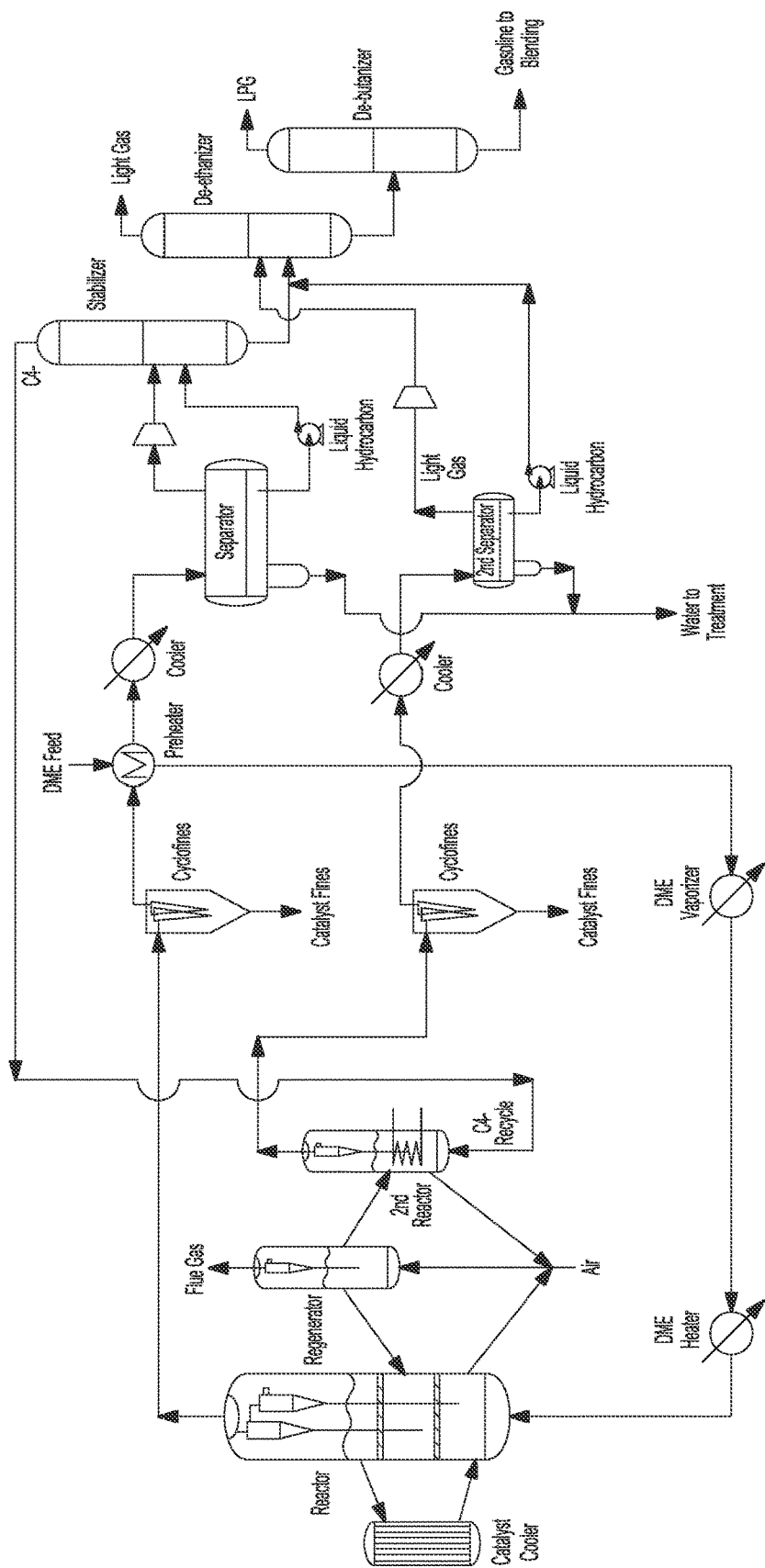
FIG. 17 illustrates an externally cooled fluidized bed process with light gas recycling to a second reactor with DME feedstock.

Additionally or alternatively to recycling to the main reactor, $C_{4-}$ light gas comprising olefins can be recycled to a different (second) reactor, e.g., to convert ethylene, propylene, and butanes to $C_{5+}$ gasoline, as shown in FIGS. 5 and 6. Heated methanol feed can be fed to the bottom of the reactor. Reactor vapor can be separated from catalyst by a set of two stage cyclones. Reactor effluent can be sent to fines collection equipment, e.g., KBR CycloFines™, to remove catalyst fines. The reactor effluent can be further cooled and partially condensed against incoming methanol feed, and then the mixed phase effluent can be sent to a water separator where the condensed aqueous phase can be separated and sent to wastewater treatment. Separator vapor and hydrocarbon liquid can be sent to a stabilizer where $C_{4-}$ light gas comprising olefins can be separated from $C_{5+}$ product. The light $C_{4-}$ gases can be recycled to a different (second) reactor, e.g., where ethylene, propylene, and butenes can be converted to $C_{5+}$ gasoline. The heat in the second reactor from the exothermic reaction can be removed by internal heat exchangers. The effluent from the second reactor after processing through a set of two stage cyclones can be sent to fines collection equipment, e.g., KBR Cyclofines™, to remove catalyst fines. The effluent from the second reactor can be further cooled and sent to a second water separator where condensed aqueous phase is separated and sent to wastewater treatment. Separator gas and hydrocarbon liquid from the second separator can be combined with $C_{5+}$ product from the stabilizer and sent to a de-ethanizer fractionating column, where $C_{2-}$ light gas can be separated from $C_{3+}$ product. The $C_{3+}$ product can be sent to a de-butanizer fractionating column where the LPG can be separated from $C_{5+}$ gasoline product. The $C_{5+}$ gasoline product can be used immediately or sent to storage for later use. The spent catalysts from the reactor can be transferred to a regenerator to regenerate the catalyst, e.g., by burning the coke off. The regenerated catalysts can then be transferred back to the reactor. In certain embodiments, a DME feed can be fed to the reactor instead of or in addition to methanol feed, as shown in FIGS. 16 and 17.

Figure 7:
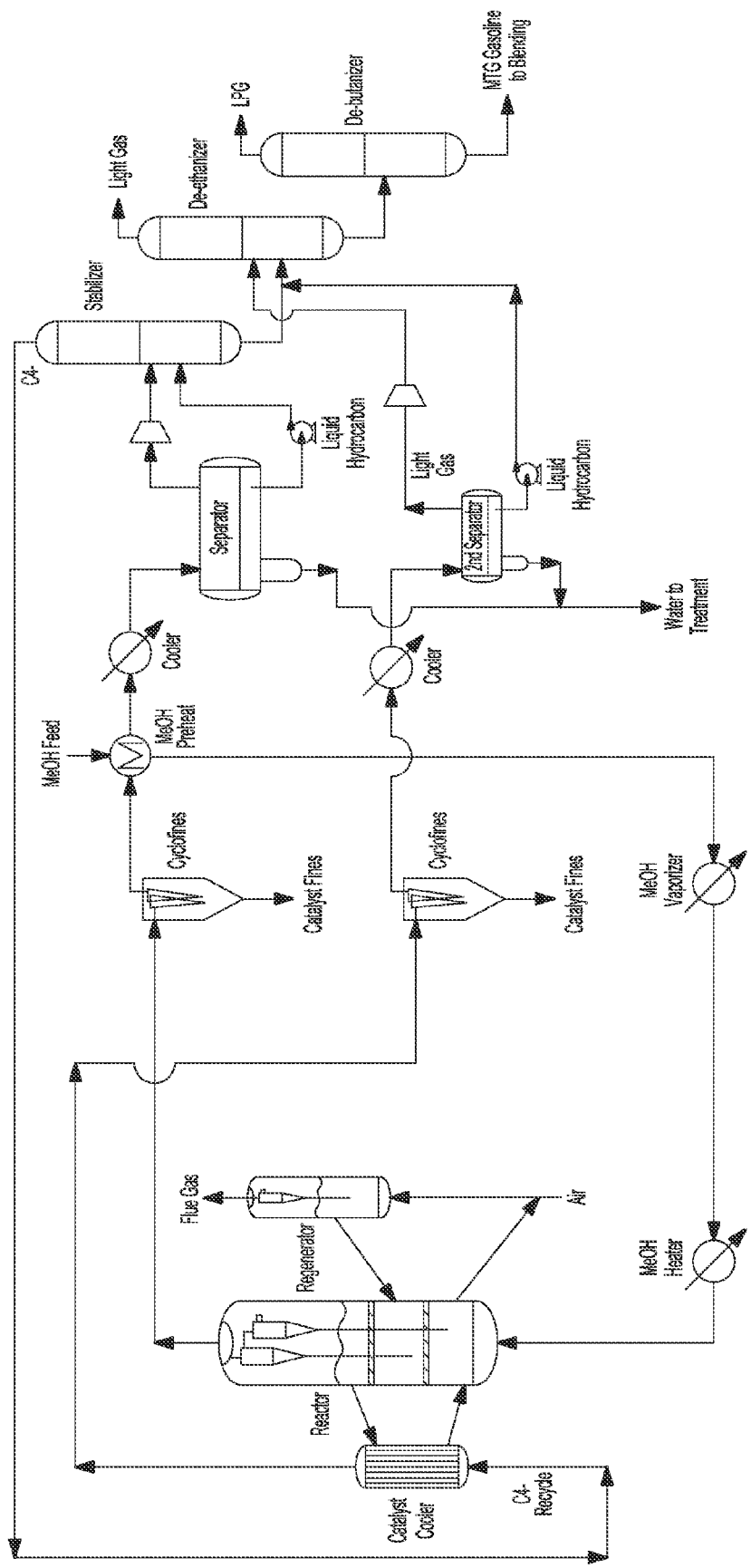
FIG. 7 illustrates an externally cooled fluidized bed MTA/MTO process with light gas recycling to a catalyst cooler.
Figure 18:
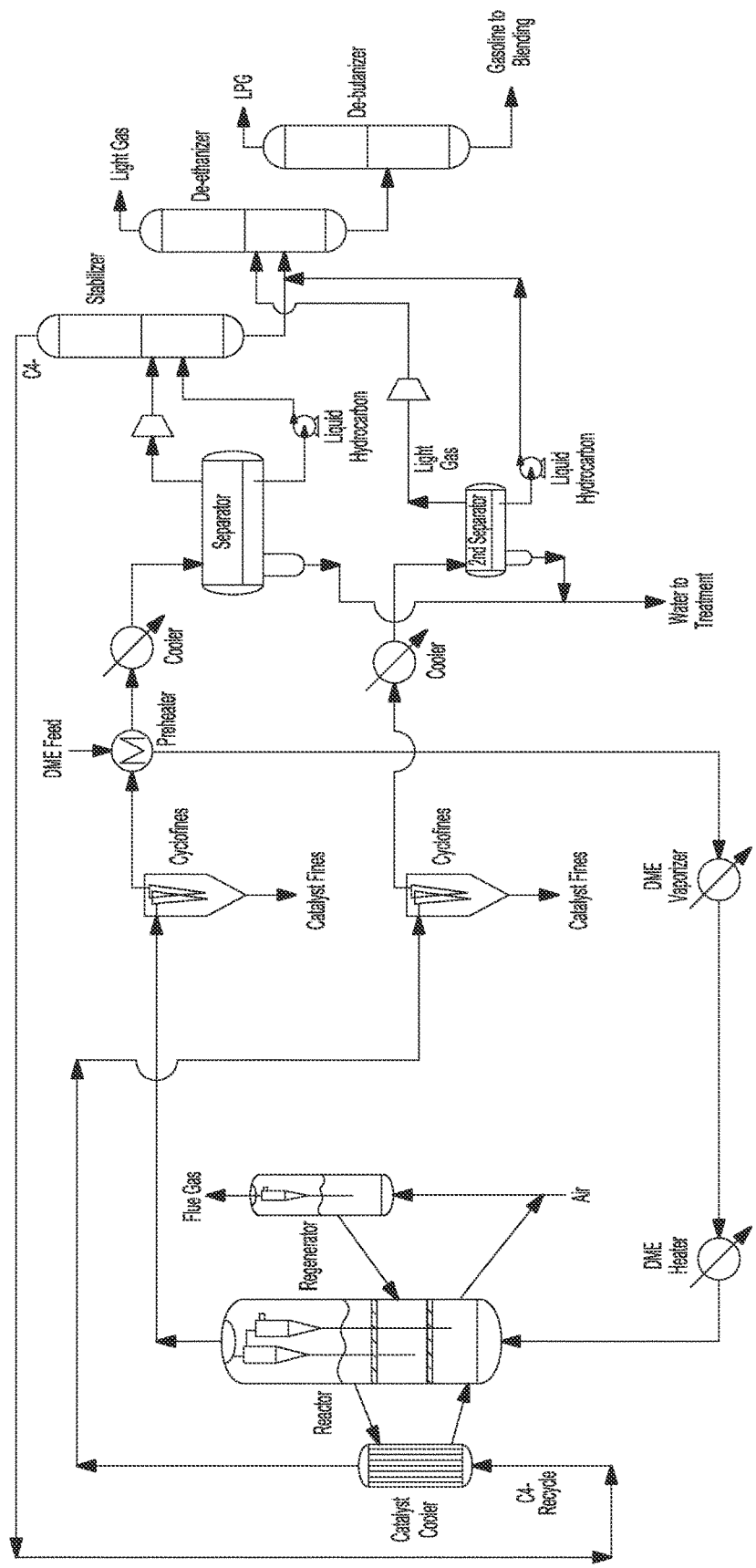
FIG. 18 illustrates an externally cooled fluidized bed process with light gas recycling to the catalyst cooler with DME feedstock.

In another embodiment, $C_{4-}$ light gas comprising olefins can be recycled to the catalyst cooler to convert ethylene, propylene, and butanes to $C_{5+}$ gasoline, as shown in FIG. 7. The heated methanol feed can be fed to the bottom of the reactor. Heat from the exothermic reaction can be removed by the external catalyst cooler. Reactor vapor can be separated from catalyst by a set of two stage cyclones. Reactor effluent can be sent to fines collection equipment, e.g., KBR CycloFines™, to remove catalyst fines. The reactor effluent can further be cooled and partially condensed against the incoming methanol feed, and then the mixed phase effluent can be sent to water separator where the condensed aqueous phase can be separated and sent to wastewater treatment. Separator vapor and hydrocarbon liquid can be sent to a stabilizer where $C_{4-}$ gases are separated from $C_{5+}$ product. $C_{4-}$ gases can be recycled to a catalyst cooler where ethylene, propylene, and butenes are converted to $C_{5+}$ gasoline. The effluent from the catalyst cooler after processing through a set of two stage cyclones can be sent to fines collection equipment, e.g., KBR Cyclofines™, to remove catalyst fines. The effluent from the catalyst cooler can further be cooled and sent to a second water separator where condensed aqueous phase can be separated and sent to wastewater treatment. Separator gas and hydrocarbon liquid from the second separator can be combined with $C_{5+}$ product from stabilizer and sent to a de-ethanizer fractionating column where $C_{2-}$ light gas can be separated from $C_{3+}$ product. The $C_{3+}$ product can be sent to a de-butanizer fractionating column where the LPG can be separated from $C_{5+}$ gasoline product. $C_{5+}$ gasoline product can be used immediately or sent to storage for later use. The spent catalysts from the reactor can be transferred to a regenerator to regenerate the catalyst by burning the coke off. The regenerated catalysts can then be transferred back to the reactor. In certain embodiments, a DME feed can be fed to the reactor instead of or in addition to methanol feed, as shown in FIG. 18.

As discussed previously, heat from the exothermic reaction in the reactor can be removed internally, for example, by internal heat exchangers, as shown in FIGS. 3, 5, 10, 14, and 16.

Additionally or alternatively, heat from the exothermic reaction in the reactor can be removed externally, for example, by an external catalyst cooler, as shown in FIGS. 4, 6, 7, 9, 11, 15, 17, and 18.

E. Alkylation

To further improve the $C_{5+}$ gasoline yield, an alkylation unit can optionally be included in the fluidized bed process to convert isobutane to $C_{5+}$ gasoline. As shown above in Table 1, $C_{5+}$ gasoline yield is about 67 wt %. With an optional alkylation unit, by recycling the isobutane, as well as the alkenes, and converting all of them to $C_{5+}$ gasoline, the $C_{5+}$ gasoline yield of a fluidized bed MTG process could be beyond 90 wt %.

Figure 8:
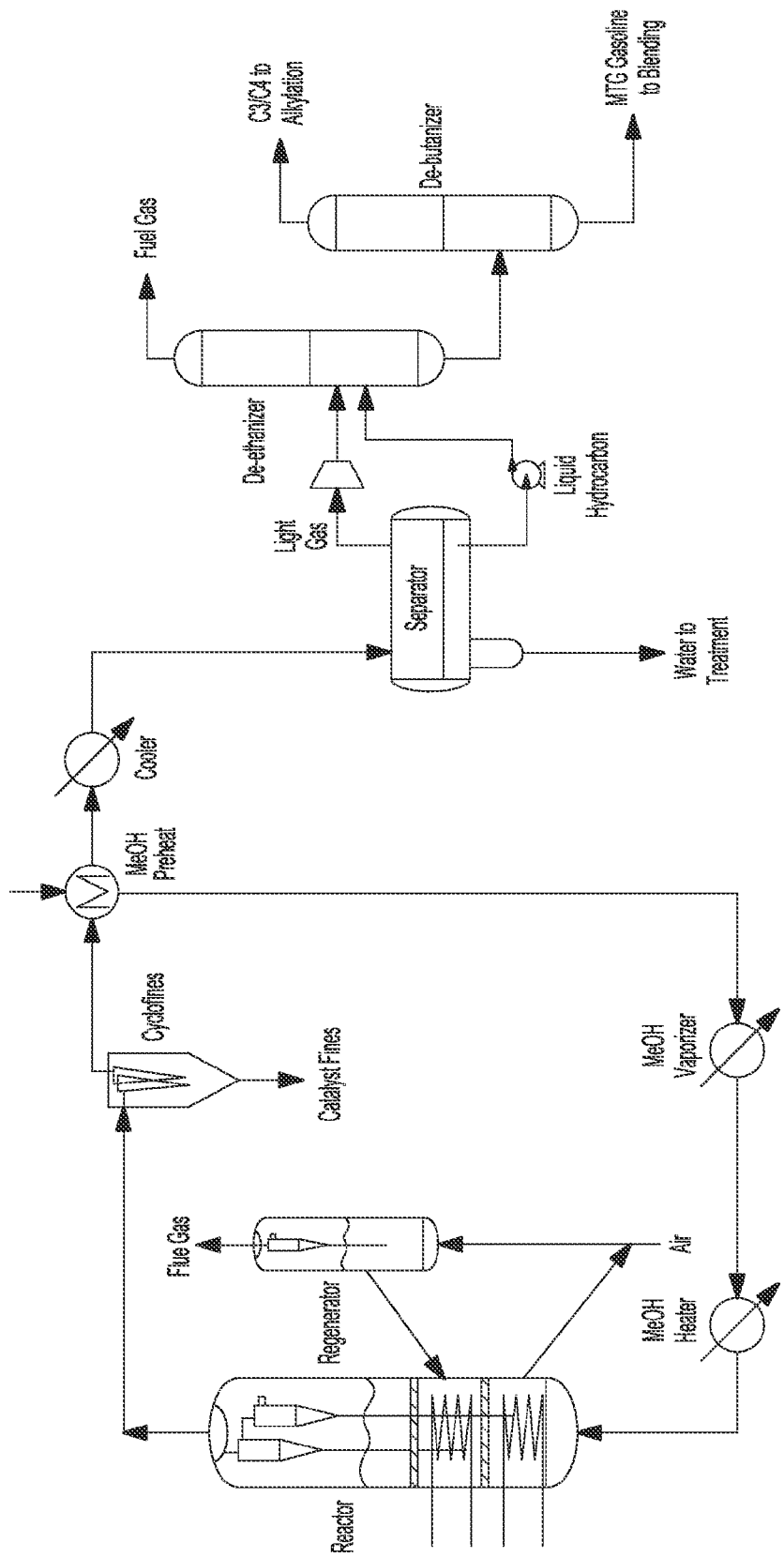
FIG. 8 illustrates an internally cooled fluidized bed MTA/MTO process with alkylation.
Figure 9:
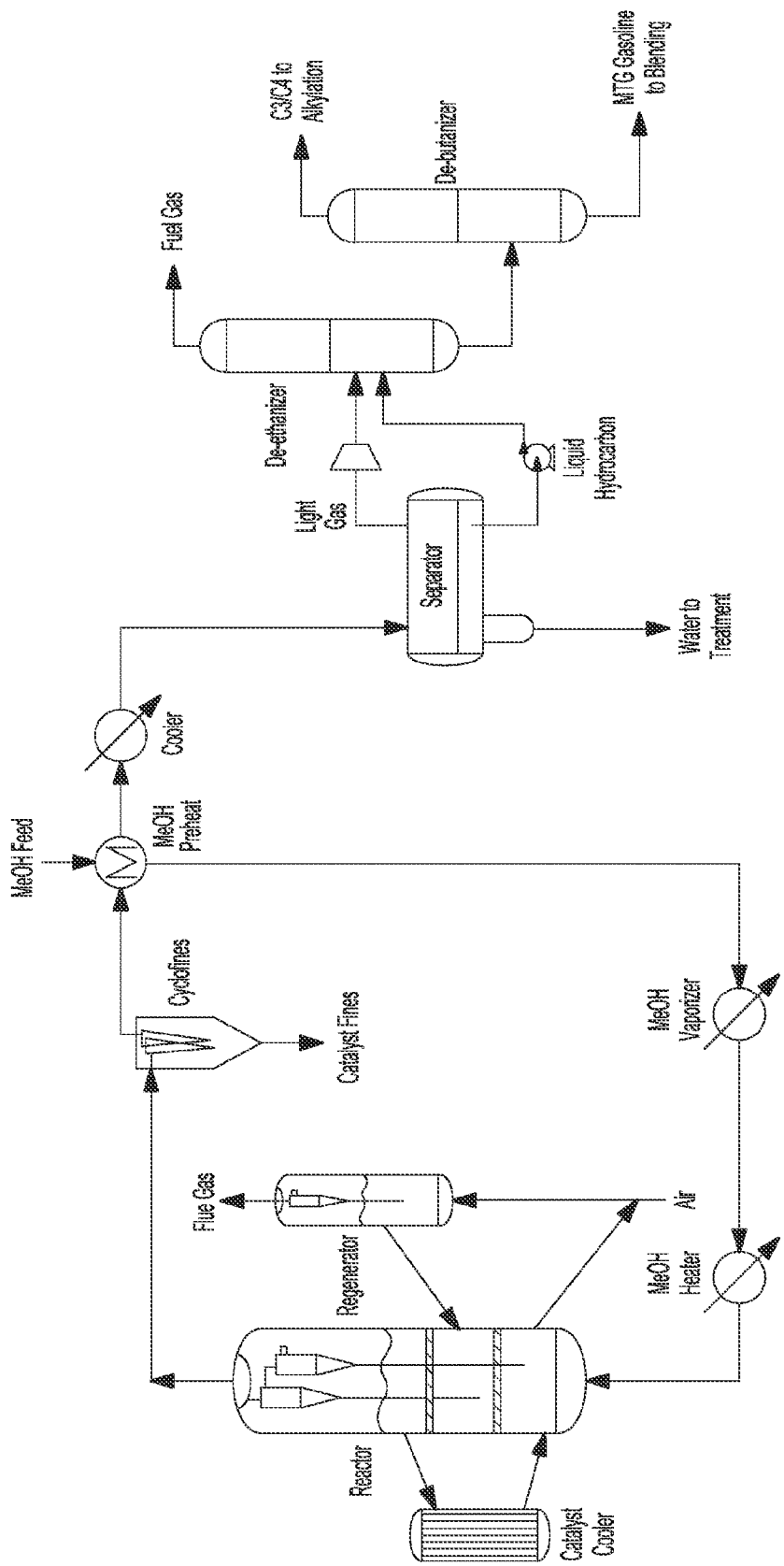
FIG. 9 illustrates an externally cooled fluidized bed MTA/MTO process with alkylation.

In a further embodiment, an alkylation unit can be included to convert isobutene, propylene, and butenes to $C_{5+}$ gasoline, as shown in FIGS. 8 and 9. The heated methanol feed can be fed to the bottom of the reactor. Reactor vapor can be separated from the catalyst by a set of two stage cyclones. Reactor effluent can be sent to fines collection equipment, e.g., KBR CycloFines™, to remove catalyst fines. The reactor effluent can be further cooled and partially condensed against the incoming methanol feed, and then the mixed phase effluent can be sent to a water separator where the condensed aqueous phase can be separated and sent to wastewater treatment. Separator vapor and hydrocarbon liquid can be sent to a de-ethanizer fractionating column where $C_{2-}$ light gas can be separated from $C_{3+}$ product. The $C_{3+}$ product can be sent to a de-butanizer fractionating column where the $C_3/C_4$ gases can be separated from $C_{5+}$ gasoline product. $C_{5+}$ gasoline product can be used immediately or sent to storage for later use. $C_3/C_4$ gases can be sent to an alkylation unit to convert isobutene, propylene, and butenes to $C_{5+}$ gasoline.

V. Production of Olefins

In another embodiment, an oxygenate is fed into a fluidized bed reactor and converted to olefins. In various aspects, the oxygenate is methanol, DME or a mixture thereof. The olefin yield of the fluid bed process can be improved by staging the reactor, operating the reactor at a higher pressure and lower temperature, and/or by providing a recycle gas stream. The spent catalysts from the reactor are transferred to the regenerator to regenerate the catalyst by burning the coke off. The regenerated catalysts are then transferred back to the reactor.

In any embodiment, the fluidized bed reactor can include at least one layer of structured packing as a staging baffle. In various aspects, the fluid bed reactor can include from one to eight layers of structured packing. Advantageously, the fluid bed reactor can include at least two layers of structured packing.

In one embodiment, the fluidized bed reactor can be internally cooled, for example with a heat exchanger that is present in at least one or each stage for cooling. Additionally or alternatively, the fluidized bed reactor is externally cooled, for example, with a catalyst cooler installed for removing the heat from the reactor by circulating the catalyst between the reactor and the cooler.

In various aspects, olefins are produced according to the processes described above for converting methanol and/or DME into $C_{5+}$ gasoline. Heated methanol feed and/or DME feed can be fed to the bottom of the reactor. Reactor vapor is separated from catalyst by a set of two stage cyclones. Reactor effluent is sent to fines collection equipment, e.g., KBR CycloFines™, to remove catalyst fines. The reactor effluent is further cooled and partially condensed against incoming methanol and/or DME feed and then the mixed phase effluent is sent to a water separator where the condensed aqueous phase is separated and sent to wastewater treatment. Separator vapor and hydrocarbon liquid are sent to a stabilizer, where $C_{4-}$ light gas comprising olefins is separated from $C_{5+}$ product. The $C_{5+}$ gasoline product is sent to storage. The spent catalysts from the reactor are transferred to a regenerator to regenerate the catalyst by burning the coke off. The regenerated catalysts are then transferred back to the reactor.

Additionally or alternatively, a recycle gas stream can be sent to either the reactor, a second reactor, or the catalyst cooler for increasing the yield of olefins.

A. Operating Conditions

The fluidized bed reactor can be operated at pressure from about 3 psig to about 450 psig, for example from about 75 psig to about 400 psig, from about 75 psig to about 300 psig, from about 75 psig to about 200 psig, from about 100 psig to about 400 psig, from about 100 psig to about 300 psig, from about 100 psig to about 200 psig, from about 150 psig to about 350 psig, at about 150 psig, at about 200 psig, or at about 250 psig. The fluidized bed reactor can be operated at a temperature from about 500° F. to about 1100° F., for example from about 700° F. to about 1100° F., from about 800° F. to about 1100° F., from about 900° F. to about 1100° F., from about 650° F. to about 1050° F., from about 650° F. to about 1000° F., from about 750° F. to about 1050° F., from about 800° F. to about 1050° F., from about 850° F. to about 1000° F., from about 850° F. to about 1050° F., from about 950° F. to about 1100° F., at about 950° F., at about 1000° F., or at about 1050° F. Further, the WHSV can be from about 0.1 kg/kg-hr to about 200 kg/kg-hr, for example from about 0.5 kg/kg-hr to about 25 kg/kg-hr, from about 1 kg/kg-hr to about 20 kg/kg-hr, or at about 1.6 kg/kg-hr, during operation.

B. Catalysts

A catalyst is used in the process described herein, which is useful for the conversion of oxygenate feeds to olefins.

The catalysts described herein can be pretreated with steam prior to use in the reactor and may contain up to 3 wt % of an element to convey steam stability, such as phosphorus and/or zinc.

In various aspects, a catalyst composition comprising a class of zeolites described in detail in U.S. Pat. Nos. 4,025,575 and 4,083,889, incorporated herein by reference, are useful for conversion of oxygenate feeds to olefins. The class of zeolites has a silica to alumina ratio of at least about 12, at least about 40, or at least about 70, and a structure providing constrained access to the crystalline free space. Additionally or alternatively, the class of zeolites has a crystal framework density, in the dry hydrogen form of not substantially below about 1.6 grams per cubic centimeter. Additionally or alternatively, the class of zeolites has a constraint index from about 1 to about 12. Examples of suitable zeolites include, but are not limited to ZSM-5, ZSM-11, ZSM-12, ZSM-21, ZSM-35, ZSM-38 and other similar material.

The zeolites useful as catalysts may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed.

Additionally or alternatively, the catalyst composition can be used in the presence of 2 moles to 20 moles, for example 3 moles to 10 moles, of steam per mol of methanol feed, as described in U.S. Pat. No. 4,083,889. The steam diluent may be provided directly by injecting the requisite amount of water or steam into the reaction zone; or it may be provided totally or in part by water mixed with the methanol feed, it being understood that the water forms steam in the reaction zone at the prescribed reaction conditions. Further, the steam diluent may be supplemented with an inert diluent selected from the group consisting of hydrogen, helium, nitrogen, carbon dioxide, a $C_1$ to $C_7$ hydrocarbon and flue gas. In such a case, up to 20 total moles of steam plus inert diluent may be used.

In other aspects, zeolites of the erionite-offretite family as described in detail in U.S. Pat. No. 4,079,095, incorporated herein by reference, are useful for conversion of oxygenate feeds to olefins. Included within this group of zeolites is erionite, both synthetic and natural, offretite, both synthetic and natural, zeolite T and zeolite ZSM-34. Additionally or alternatively, these zeolites may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

In another aspect, catalyst compositions comprising the zeolite, ZSM-48, as described in detail in U.S. Pat. No. 4,476,338, incorporated herein by reference, are useful for conversion of oxygenate feeds to olefins.

In still other aspects, catalyst compositions comprising silicoaluminophosphate (SAPO) molecular sieves as described in detail in U.S. Pat. No. 4,677,242, incorporated herein by reference, are useful for conversion of oxygenate feeds to olefins. Examples of useful SAPO molecular sieves include but are not limited to SAPO-5, SAPO-11, SAPO-16, SAPO-17, SAPO-20, SAPO-31, SAPO-34, SAPO-35, SAPO-37, SAPO-40, SAPO-41, SAPO-42 and SAPO-44.

In still other aspects, catalyst compositions comprising non-zeolitic molecular sieves as described in detail in U.S. Pat. No. 4,752,651, incorporated herein by reference, are useful for conversion of oxygenate feeds to olefins. Examples of useful non-zeolitic molecular sieves include but are not limited to ELAPSO, metal aluminophosphates (MeAPOs where "Me" is at least one of Mg, Mn, Co and Zn), ferroaluminophosphates (FeAPO or FAPO), titanium aluminophosphates (TAPO), ELAPO, TiAPSO, MgAPSO, MnAPSO, CoAPSO, ZnAPSO, FeAPSO, CoMnAPSO and CoMnMgAPSO molecular sieves as described in U.S. Pat. No. 4,752,641.

VI. Production of Aromatics

In certain embodiments, an oxygenate is fed into a fluidized bed reactor and converted to aromatics. In various aspects, the oxygenate can comprise or be methanol and/or DME. The aromatic yield of the fluid bed process can be improved by staging the reactor, operating the reactor at a higher pressure and lower temperature, and/or by providing a recycle gas stream. The spent catalysts from the reactor can be transferred to the regenerator to regenerate the catalyst by burning the coke off. The regenerated catalysts can then be transferred back to the reactor.

In any embodiment, the fluidized bed reactor can include at least one layer of structured packing as a staging baffle. In various aspects, the fluid bed reactor can include from one to eight layers of structured packing. Advantageously, the fluid bed reactor can include at least two layers of structured packing.

In certain embodiments, the fluidized bed reactor can be internally cooled, for example with a heat exchanger that is present in at least one or each stage for cooling. Additionally or alternatively, the fluidized bed reactor can be externally cooled, for example, with a catalyst cooler installed for removing the heat from the reactor by circulating the catalyst between the reactor and the cooler.

In various aspects, aromatics can be produced according to the processes described above for converting methanol and DME into $C_{5+}$ gasoline. Heated methanol feed and/or DME feed can be fed to the bottom of the reactor. Reactor vapor can be separated from catalyst by a set of two stage cyclones. Reactor effluent can be sent to fines collection equipment, e.g., KBR CycloFines™, to remove catalyst fines. The reactor effluent can be further cooled and partially condensed against incoming methanol and/or DME feed, and then the mixed phase effluent can be sent to a water separator where the condensed aqueous phase can be separated and optionally sent to wastewater treatment. Aromatics can be separated from the separator vapor and hydrocarbon liquid and sent to storage. The spent catalysts from the reactor can be transferred to a regenerator to regenerate the catalyst by burning the coke off. The regenerated catalysts can then be transferred back to the reactor.

Additionally or alternatively, a recycle gas stream can be sent to the reactor, to a second reactor, or to the catalyst cooler for increasing the yield of aromatics.

A. Operating Conditions

The fluidized bed reactor can be operated at pressure from about 3 psig to about 450 psig, such as about 35 psig. The fluidized bed reactor can be operated at a temperature of about 500° F. to about 1100° F., such as about 1000° F. Further, the WHSV can be from about 0.1 to about 200, for example about 1.6, during operation.

B. Catalysts

A zeolite catalyst composition can be used for the conversion of oxygenate feeds to aromatics. While some catalyst compositions include a binder, in other cases, the catalyst composition may be referred to as being "self-bound" or "unbound." The terms "unbound" and "self-bound" are intended to be synonymous and mean that such a catalyst composition is free of any inorganic oxide binders, such as alumina and/or silica, which are frequently combined with zeolite catalysts to enhance their physical properties.

The catalysts described herein can be pretreated with steam prior to use in the reactor.

A zeolite employed in the present catalyst composition can generally comprise at least one medium pore aluminosilicate zeolite or silica aluminophosphate (SAPO) having a Constraint Index of 1-12. The Constraint Index may be ≤about 12, ≤about 11, ≤about 10, ≤about 9, ≤about 8, ≤about 7, ≤about 6, ≤about 5, ≤about 4, ≤about 3, or ≤about 2. Additionally or alternatively, the Constraint Index may be about ≥about 11, ≥about 10, ≥about 9, ≥about 8, ≥about 7, ≥about 6, ≥about 5, ≥about 4, ≥about 3, ≥about 2, or ≥about 1. In any embodiment, the Constraint Index may be 1 to about 10, 1 to about 8, 1 to about 6, 1 to about 5, 1 to about 3, about 2 to about 11, about 3 to about 10, about 4 to about 9, or about 6 to about 9, etc. Constraint Index is determined as described in U.S. Pat. No. 4,016,218, incorporated herein by reference for details of the method. Suitable zeolites include zeolites having an MFI or MEL framework, such as ZSM-5 or ZSM-11.

Some useful catalysts compositions can include a zeolite having a structure wherein there is at least one 10-member ring channel and no channel of rings having more than 10 members. Some such molecular sieves may be referred to as having a framework type or topology of EUO, FER, IMF, LAU, MEL, MRI, MFS, MTT, MWW, NES, PON, SFG, STF, STI, TUN, or PUN. Particularly useful zeolites can have a BEA, MFI, or MEL framework type.

Non-limiting examples of SAPOs useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

Particular other zeolites useful in embodiments of the invention can include ZSM-5, ZSM-11; ZSM-12; ZSM-22; ZSM-23; ZSM-34, ZSM-35; ZSM-48; ZSM-57; and/or ZSM-58. Other useful zeolites may additionally or alternately include MCM-22, PSH-3, SSZ-25, MCM-36, MCM-49 or MCM-56, with MCM-22. In any embodiment the zeolite may comprise or be ZSM-5 or ZSM-11. ZSM-5 is described in detail in U.S. Pat. Nos. 3,702,886 and RE 29,948. ZSM-11 is described in detail in U.S. Pat. No. 3,709,979. ZSM-5 can be particularly useful.

Generally, a zeolite having the desired activity can have a silicon to aluminum molar ratio of about 10 to about 300. In any embodiment, the molar ratio of silicon to aluminum may be ≤about 300, ≤about 200, ≤about 150, ≤about 125, ≤about 100, ≤about 80, ≤about60, ≤about 50, ≤about 40, about 30, ≤about 25, ≤about 20, ≤about ≤15 or about ≤10. Additionally or alternatively, the molar ratio of silicon to aluminum may be ≥about 10, ≥about 15, ≥about 20, ≥about 25, ≥about 30, ≥about 40, ≥about 50, ≥about 60, ≥about 80, ≥about 100, ≥about 125, ≥about 150, or ≥about 200; e.g., 20 to about 200, about 30 to about 100, about 40 to about 80, about 50 to about 50, about 15 to about 100, or about 20 to about 40.

In some preferred aspects, the silicon to aluminum ratio can be at least about 20, such as at least about 30 or at least about 40. In such embodiments, the silicon to aluminum ratio can optionally be about 80 or less, such as about 60 or less, or about 50 or less, or about 40 or less. Typically, reducing the molar ratio of silicon to aluminum in a zeolite can result in a zeolite with a higher acidity, and therefore in higher activity for cracking of hydrocarbon or hydrocarbonaceous feeds, such as petroleum feeds. However, with respect to conversion of oxygenates to aromatics, such increased cracking activity may not be beneficial, and instead may result in increased formation of residual carbon or coke during the conversion reaction. Such residual carbon or coke can deposit on the zeolite catalyst, leading to deactivation of the catalyst over time. Having a molar ratio of silicon to aluminum of ≥about 40, such as ≥about 50 or ≥about 60, can reduce and/or minimize the amount of additional residual carbon formed due to the acidic or cracking activity of the catalyst.

It is noted that the molar ratio described herein is a ratio of silicon to aluminum. If a corresponding ratio of silica to alumina is described, the corresponding ratio of silica ($SiO_2$) to alumina ($Al_2O_3$) would be twice as large, due to the presence of two aluminum atoms in each alumina stoichiometric unit. Thus, a molar ratio of silicon to aluminum of 10 corresponds to a silica to alumina ratio of 20.

When used in the present catalyst compositions, the zeolite can be present at least partly in the hydrogen (acid, active) form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of about 400° C. to about 700° C. to convert the ammonium form to the (active) hydrogen form.

Zeolite catalyst compositions can include and/or be enhanced by a transition metal. Catalyst compositions herein can include a Group 10-12 element, or combinations thereof, of the Periodic Table. Exemplary Group 10 elements can include, nickel, palladium, and/or platinum, particularly nickel. Exemplary Group 11 elements can include copper, silver, and/or gold, particularly copper. Exemplary Group 12 elements can include, e.g., zinc and/or cadmium. Advantageously, the transition metal can comprise or be a Group 12 metal from the periodic table (sometimes designated as Group IIB) such as Zn and/or Cd. In particular embodiments, nickel, copper and/or zinc, particularly zinc, may be used. The Group 10-12 element can be incorporated into the zeolite by any convenient method, such as by impregnation or by ion exchange. After such incorporation, the Group 10-12 element-enhanced catalyst can be treated in an oxidizing environment (air) or an inert atmosphere at a temperature of about 400° C. to about 700° C.

The amount of Group 10-12 element can be related to the molar amount of aluminum present in the zeolite. In certain embodiments, the molar ratio of the Group 10-12 element to aluminum in the zeolite can be about 0.1 to about 1.3. For example, the molar ratio of the Group 10-12 element to aluminum in the zeolite can be about ≥0.1, e.g., ≥about 0.2, ≥about 0.3, or ≥about 0.4. Additionally or alternatively, the molar ratio of the Group 10-12 element to aluminum in the zeolite can be about ≤1.3, such as about ≤1.2, ≤about 1.0, or ≤about 0.8. In any embodiment, the ratio of the Group 10-12 element to aluminum is about 0.2 to about 1.2, about 0.3 to about 1.0, or about 0.4 to about 0.8. Still further additionally or alternatively, the amount of Group 10-12 element can be expressed as a weight percentage of the self-bound or unbound zeolite, such as having ≥about 0.1 wt %, ≥about 0.25 wt %, ≥about 0.5 wt %, ≥about 0.75 wt %, or ≥about 1.0 wt % of Group 10-12 element. Additionally or alternatively, the amount of Group 10-12 element can be present in an amount of ≤about 20 wt %, such as ≤about 10 wt %, ≤about 5 wt %, ≤about 2.0 wt %, ≤about 1.5 wt %, ≤about 1.2 wt %, ≤about 1.1 wt %, or ≤about 1.0 wt %. In any embodiment, the amount of Group 10-12 element may be about 0.25 to about 10 wt %, about 0.5 to about 5.0 wt %, about 0.75 to about 2.0 wt %, or about 1.0 to about 1.5 wt %, based on the total weight of the catalyst composition excluding the weight of any binder if present.

The catalyst compositions can optionally also include a Group 15 element, e.g., phosphorous, arsenic, antimony, bismuth, and combinations thereof, in addition to the transition metal, particularly phosphorous.

The Group 15 element can be incorporated into the catalyst composition in any of the same manners described for incorporation of the Group 10-12 element. Any source of convenient source of the Group 15 element may be used, e.g., phosphoric acid ($H_3PO_4$) or ammonium dihydrogen phosphate ($NH_4H_2PO_4$). Typically, the catalyst composition can have a molar ratio of Group 15 to Group 10-12 element of about 0.1 to about 10. In any embodiment, the molar ratio of Group 15 to Group 10-12 element may be ≤about 10, ≤about 9.0, ≤about 8.0, ≤about 7.0, ≤about 6.0, ≤about 5.0, ≤about 4.0, ≤about 3.0, ≤about 2.5, ≤about 1.0, ≤about 0.5, ≤about 0.4, ≤about 0.3, ≤about 0.2, or ≤about 0.1. Additionally or alternatively, the molar ratio of Group 15 to Group 10-12 element may be ≥about 0.1, ≥about 0.2, ≥about 0.3, ≥about 0.4, ≥about 0.5, ≥about 1.5, ≥about 2.0, ≥about 3.0, ≥about 4.0, ≥about 5.0, ≥about 6.0, ≥about 7.0, ≥about 8.0, ≥about 9.0, or ≥about 10. Ranges of the molar ratio of Group 15 to Group 10-12 element expressly disclosed include combinations of any of the above-enumerated upper and lower limits, e.g., about 0.2 to about 9.0, about 0.4 to about 8.0, about 0.6 to about 6.0, about 0.8 to about 4.0, about 1.0 to about 3.0, about 1.5 to about 2.5, etc. Additionally or alternatively, the amount of Group 15 element can be present in an amount of about ≤5.0 wt %, such as ≤about 2.5 wt %, ≤about 1.0 wt %, ≤about 0.75 wt %, ≤about 0.50 wt %, ≤about 0.25 wt %, or ≤about 0.1 wt %. In any embodiment, the amount of Group 15 element may be about 0.1 to about 5.0 wt %, about 0.25 to about 2.0 wt %, about 0.5 to about 1.0 wt %, or about 1.0 wt %, based on the total weight of the catalyst composition excluding the weight of any binder if present. Where the zeolite is a SAPO and the Group 15 element includes phosphorous, the molar amounts and weight percentages of the phosphorous recited in this paragraph shall exclude the amount of phosphorous attributed to the SAPO zeolite.

In one embodiment, the catalyst can be modified with up to about 3 wt % phosphorous for improved stability and up to about 3 wt % zinc for improved aromatics yield.

Additionally or alternately, the catalyst composition can be substantially free of phosphorous. A catalyst composition substantially free of phosphorous can contain about 0.01 wt % of phosphorous or less, such as less than about 0.005 wt % or less than about 0.001 wt % of phosphorous. A catalyst composition substantially free of phosphorous can be substantially free of intentionally added phosphorous or substantially free of both intentionally added phosphorous as well as phosphorous present as an impurity in a reagent for forming the catalyst composition. Additionally or alternately, the catalyst composition can contain no added phosphorous, such as containing no intentionally added phosphorous and/or containing no phosphorous impurities to within the detection limits of standard methods for characterizing a reagent and/or a resulting zeolite.

Additionally or alternatively, the catalyst compositions may include at least one Group 2 and/or a Group 3 element. As used herein the term "Group 3" is intended to include elements in the Lanthanide series of the Periodic Table. In any embodiment, one or more Group 2 elements (e.g., Be, Mg, Ca, Sr, Ba and Ra) may be used. In other embodiments, one or more Group 3 elements (e.g., Sc and Y) can be used, including or comprising a Lanthanide (e.g., La, Ce, Pr, Nd, Sm, Eu, Gd, Tb, Dy, Ho, Er, Tm, Yb, and Lu). While an Actinide may be used, such elements are not believed to offer any particular advantage. When present, the total weight of the at least one Group 2 and/or Group 3 elements can be from about 0.1 to about 20 wt %, based on the total weight of the catalyst composition excluding the weight of any binder if present. In any embodiment, the amount of the at least one Group 2 and/or a Group 3 element may be about 0.25 to about 10 wt %, about 0.5 to about 5.0 wt %, about 0.75 to about 2.0 wt %, or about 1.0 to about 1.5 wt %. The presence of Group 2 and/or Group 3 element is believed to help reduce coke formation.

The catalyst composition can employ the zeolite in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Advantageously, the Group 15 element, the Group 10-12 element, and/or the at least one Group 2 and/or Group 3 element can be incorporated after formulation of the zeolite (such as by extrusion) to form self-bound catalyst particles. Optionally, a self-bound catalyst can be steamed after extrusion.

Thus, embodiments of the catalyst compositions described herein can further be characterized by at least one, for example at least two, or advantageously all, of the following properties:

(a) a mesoporosity (i.e., mesoporous surface area or surface area external to the zeolite) of ≥about 20 $m^2/g$, e.g., ≥about 30 $m^2/g$, ≥about 40 $m^2/g$, ≥about 50 $m^2/g$, ≥about 60 $m^2/g$, ≥about 70 $m^2/g$, ≥about 80 $m^2/g$, ≥about 90 $m^2/g$, ≥about 100 $m^2/g$, or ≥about 200 $m^2/g$. Additionally or alternatively, the mesoporous surface area may be ≤about 500 $m^2/g$, e.g., ≤about 400 $m^2/g$, ≤about 300 $m^2/g$, ≤about 200 $m^2/g$, or ≤about 100 $m^2/g$. Exemplary such ranges for the mesoporous surface can include about 20 to 500 $m^2/g$, about 20 to about 400 $m^2/g$, about 20 to about 300 $m^2/g$, about 20 to about 200 $m^2/g$, about 20 to about 100 $m^2/g$, about 20 to about 90 $m^2/g$, about 20 to about 80 $m^2/g$, about 20 to about 70 $m^2/g$, about 20 to about 60 $m^2/g$, about 20 to about 50 $m^2/g$, about 30 to about 200 $m^2/g$, about 30 to about 100 $m^2/g$, about 40 to about 100 $m^2/g$, about 50 to about 100 $m^2/g$, about 60 to about 100 $m^2/g$, about 70 to about 100 $m^2/g$, etc.;

(b) a microporous surface area of ≥about 100 $m^2/g$, e.g., ≥about 200 $m^2/g$, ≥about 300 $m^2/g$, ≥about 340 $m^2/g$, ≥about 350 $m^2/g$, ≥about 360 $m^2/g$, or ≥about 370 $m^2/g$. Additionally or alternatively, the microporous surface area may be ≤about 1000 $m^2/g$, e.g., ≤about 750 $m^2/g$, ≤about 600 $m^2/g$, or ≤about 500 $m^2/g$. Exemplary such ranges can include about 100 to about 1000 $m^2/g$, about 200 to about 1000 $m^2/g$, about 300 to about 1000 $m^2/g$, about 340 to about 1000 $m^2/g$, about 350 to about 1000 $m^2/g$, about 360 to about 1000 $m^2/g$, about 370 to about 1000 $m^2/g$, about 100 to about 750 $m^2/g$, about 200 to about 750 $m^2/g$, about 300 to about 750 $m^2/g$, about 340 to about 750 $m^2/g$, about 350 to about 750 $m^2/g$, about 360 to about 750 $m^2/g$, about 370 to about 750 $m^2/g$, about 360 to about 600 $m^2/g$, or about 350 to about 500 $m^2/g$, etc.; and/or (c) a diffusivity for 2,2-dimethylbutane of ≥about $1.0 \times 10^{-2}$ $sec^{-1}$, e.g., ≥about $1.10 \times 10^{-2}$ $sec^{-1}$, ≥about $1.15 \times 10^{-2}$ $sec^{-1}$, ≥about $1.20 \times 10^{-2}$ $sec^{-1}$, ≥about $1.25 \times 10^{-2}$ $sec^{-1}$, or ≥about $1.50 \times 10^{-2}$ $sec^{-1}$ Additionally or alternatively, the diffusivity for 2,2-dimethylbutane may be ≤about $3.00 \times 10^{-2}$ $sec^{-1}$, ≤about $2.75 \times 10^{-2}$ $sec^{-1}$, ≤about $2.50 \times 10^{-2}$ $sec^{-1}$ or ≤about $2.00 \times 10^{-2}$ $sec^{-1}$. Exemplary such ranges can include about $1.0 \times 10^{-2}$ $sec^{-1}$ to about $3.00 \times 10^{-2}$ $sec^{-1}$, about $1.25 \times 10^{-2}$ to about $3.00 \times 10^{-2}$ $sec^{-1}$, about $1.50 \times 10^{-2}$ to about $2.00 \times 10^{-2}$ $sec^{-1}$, etc., when measured at a temperature of about 120° C. and a 2,2-dimethylbutane pressure of about 60 torr (about 8 kPa).

Of these properties, mesoporosity and diffusivity for 2,2-dimethylbutane are determined by a number of factors for a given zeolite, including the crystal size of the zeolite. Microporous surface area is determined by the pore size of the zeolite and the availability of the zeolite pores at the surfaces of the catalyst particles. Producing a zeolite catalyst with the desired low (minimum) mesoporosity, microporous surface area, and 2,2-dimethylbutane diffusivity would be well within the expertise of anyone of ordinary skill in zeolite chemistry. It is noted that mesopore surface area and micropore surface area can be characterized, for example, using adsorption-desorption isotherm techniques within the expertise of one of skill in the art, such as the BET (Brunauer Emmet Teller) method.

It is noted that the micropore surface area can be characterized for zeolite crystals or a catalyst formed from the zeolite crystals. In various aspects, the micropore surface area of a self-bound catalyst or a catalyst formulated with a separate binder can be ≥about 100 $m^2/g$, e.g., ≥about 200 $m^2/g$, ≥about 300 $m^2/g$, ≥about 340 $m^2/g$, ≥about 350 $m^2/g$, ≥about 360 $m^2/g$, or ≥about 370 $m^2/g$. Additionally or alternatively, the microporous surface area may be ≤about 1000 $m^2/g$, e.g., ≤about 750 $m^2/g$, ≤about 600 $m^2/g$, or ≤about 500 $m^2/g$. Exemplary such ranges can include about 100 to about 1000 $m^2/g$, about 200 to about 1000 $m^2/g$, about 300 to about 1000 $m^2/g$, about 340 to about 1000 $m^2/g$, about 350 to about 1000 $m^2/g$, about 360 to about 1000 $m^2/g$, about 370 to about 1000 $m^2/g$, about 100 to about 750 $m^2/g$, about 200 to about 750 $m^2/g$, about 300 to about 750 $m^2/g$, about 340 to about 750 $m^2/g$, about 350 to about 750 $m^2/g$, about 360 to about 750 $m^2/g$, about 370 to about 750 $m^2/g$, about 360 to about 600 $m^2/g$, or about 350 to about 500 $m^2/g$, etc. Typically, a formulation of zeolite crystals into catalyst particles (either self-bound or with a separate binder) can result in some loss of micropore surface area relative to the micropore surface area of the zeolite crystals. Thus, in order to provide a catalyst having the desired micropore surface area, the zeolite crystals can also have a micropore surface area of ≥about 100 $m^2/g$, e.g., ≥about 200 $m^2/g$, ≥about 300 $m^2/g$, ≥about 340 $m^2/g$, ≥about 350 $m^2/g$, ≥about 360 $m^2/g$, or ≥about 370 $m^2/g$. Additionally or alternatively, the microporous surface area may be ≤about 1000 $m^2/g$, e.g., ≤about 750 $m^2/g$, ≤about 600 $m^2/g$, or ≤about 500 $m^2/g$. Exemplary such ranges can include about 100 to about 1000 $m^2/g$, about 200 to about 1000 $m^2/g$, about 300 to about 1000 $m^2/g$, about 340 to about 1000 $m^2/g$, about 350 to about 1000 $m^2/g$, about 360 to about 1000 $m^2/g$, about 370 to about 1000 $m^2/g$, about 100 to about 750 $m^2/g$, about 200 to about 750 $m^2/g$, about 300 to about 750 $m^2/g$, about 340 to about 750 $m^2/g$, about 350 to about 750 $m^2/g$, about 360 to about 750 $m^2/g$, about 370 to about 750 $m^2/g$, about 360 to about 600 $m^2/g$, or about 350 to about 500 $m^2/g$, etc. As a practical matter, the micropore surface area of a zeolite crystal and/or a corresponding self-bound or bound catalyst as described herein can be ≤about 1000 $m^2/g$, and typically ≤about 750 $m^2/g$. Additionally or alternatively, the micropore surface area of a catalyst (self-bound or with a separate binder) can be ≤about 105% of the micropore surface area of the zeolite crystals in the catalyst, and typically ≤about 100% of the micropore surface area of the zeolite crystals in the catalyst, such as from about 80% to about 100% of the micropore surface area of the zeolite crystals in the catalyst. For example, the micropore surface area of a catalyst can be ≥about 80% of the micropore surface area of the zeolite crystals in the catalyst, such as ≥about 85%, ≥about 90%, ≥about 95%, ≥about 97%, or ≥about 98%, and/or ≤about 100%, ≤about 99%, ≤about 98%, ≤about 97%, or ≤about 95%.

Additionally or alternatively, the diffusivity for 2,2-dimethylbutane of a catalyst composition (self-bound or with a separate binder) can be ≤about 105% of the diffusivity for 2,2-dimethylbutane of the zeolite crystals in the catalyst, and typically ≤about 100% or of the diffusivity for 2,2-dimethylbutane of the zeolite crystals in the catalyst, such as from about 80% to about 100% of the diffusivity for 2,2-dimethylbutane of the zeolite crystals in the catalyst. For example, the diffusivity for 2,2-dimethylbutane of a catalyst can be ≥about 80% of the diffusivity for 2,2-dimethylbutane of the zeolite crystals in the catalyst, such as ≥about 85%, ≥about 90%, ≥about 95%, ≥about 97%, or ≥about 98%, and/or ≤about 100%, ≤about 99%, ≤about 98%, ≤about 97%, or ≤about 95%.

Additionally or alternatively, the catalyst composition comprises particles having a size ≥about 0.01 µm, ≥about 0.05 µm, ≥about 0.08 µm, ≥about 0.10 µm, ≥about 0.20 µm, or ≥about 0.50 µm. Likewise, the catalyst composition may comprise particles wherein the upper limit is ≤about 0.6 µm, ≤about 0.5 µm, ≤about 0.4 µm, ≤about 0.3 µm, ≤about 0.2 µm, ≤about 0.1 µm, or ≤about 0.05 µm. In any embodiment, the catalyst may comprise particles having a size of about 0.01 µm to about 0.6 µm, about 0.02 to about 0.50 µm, about 0.03 to about 0.40 µm etc. As used herein the term "size" means either the diameter of approximately spherical particles or, where a particle has another shape, the average of the longest dimension and the dimension orthogonal thereto. Particle dimensions and size can be determined by any suitable means, typically microscopically, using a representative number of particles. "Size" may refer to self-bound particles or particles including a binder, or those formed by extrusion of other method.

Additionally or alternatively, catalyst compositions herein may be described by a particle size distribution, $D_x$, ≤about 1.0 µm, ≤about 0.5 µm, ≤about 0.40 µm, ≤about 0.20 µm, ≤about 0.10 µm, ≤about 0.05 µm, or ≤about 0.01 µm, where x is 50, 90, or 95. The particle size distribution, may also be ≥about 1.0 µm, ≥about 0.8 µm, ≥about 0.5 µm, ≥about 0.20 µm, ≥about 0.10 µm, ≥about 0.05 µm, ≥about 0.01 µm. In any embodiment, the particle size distribution, $D_x$, may be about 0.01 to about 0.60 µm, about 0.02 to about 0.50 µm, about 0.03 to about 0.40 µm, about 0.01 to about 0.05 µm, about 0.10 to about 0.60 µm, about 0.2 to about 0.5 µm, or about 0.3 to about 0.4 µm. The particle size distribution, $D_x$, means that at least x number percent of the particles have a size, as defined above, in the recited range. For example, a catalyst composition described as having a $D_{90}$ of 0.10 to 0.60 means that at least 90 number percent of the particles have a size between 0.10 and 0.60 µm. In any embodiment, the particle size may be relatively narrow, i.e., $D_{90}$ or $D_{95}$ may be preferred, i.e., a $D_{90}$ or $D_{95}$ of ≤about 1 µm, ≤about 0.5 µm, or ≤about 0.4 µm, about 0.01 to about 0.60 µm, about 0.02 to about 0.50 µm, about 0.03 to about 0.40 µm, about 0.01 to about 0.05 µm, about 0.10 to about 0.60 µm, about 0.2 to about 0.5 µm, or about 0.30 to about 0.40 µm.

In some aspects, the catalyst composition can have an alpha value of at least about 10, such as at least about 20 or at least about 50. Additionally or alternatively, the catalyst composition can have an alpha value of ≤about 1000, ≤about 800, ≤about 700, or ≤about 600; e.g., about 10 to about 1000, about 10 to about 800, or about 50 to 700. The alpha value of a catalyst composition is a measure of the acid activity of a zeolite catalyst as compared with a standard silica-alumina catalyst. The alpha test is described in U.S. Pat. No. 3,354,078; in the Journal of Catalysis at vol. 4, p. 527 (1965), vol. 6, p. 278 (1966), and vol. 61, p. 395 (1980), each incorporated herein by reference as to that description. The experimental conditions of the test used herein include a constant temperature of about 538° C. and a variable flow rate as described in detail in the Journal of Catalysis at vol. 61, p. 395. The higher alpha values correspond with a more active cracking catalyst.

Catalyst Binders

A catalyst composition as described herein can employ a transition metal-enhanced zeolite in its original crystalline form, or the crystals can be formulated into catalyst particles, such as by extrusion. One example of binding zeolite crystals to form catalyst particles is to form a self-bound catalyst. A process for producing zeolite extrudates in the absence of a binder is disclosed in, for example, U.S. Pat. No. 4,582,815, the entire contents of which are incorporated herein by reference.

As another example of forming a self-bound catalyst, the following procedure describes a representative method for forming self-bound ZSM-5 catalyst particles. It is noted that the absolute values in grams provided below should be considered as representative of using an appropriate ratio of the various components. ZSM-5 crystal (such as about 1,400 grams on a solids basis) can be added to a mixer and dry mulled. Then, (approximately 190 grams of deionized) water can be added during mulling. After about 10 minutes, (about 28 grams of about 50 wt %) caustic (solution) mixed with (about 450 grams of deionized) water can be added to the mixture and mulled for an additional about 5 minutes. The mixture can then be extruded into (~1/10") quadralobes. The extrudates can be dried overnight (for about 8-16 hours at about 250° F. (about 121° C.)) and then calcined in nitrogen (for about 3 hours at about 1000° F. (about 538° C.)). The extrudates can then be exchanged twice with (an ~1N solution of) ammonium nitrate. The exchanged crystal can be dried overnight (for about 8-16 hours at about 250° F. (about 121° C.)) and then calcined in air (for about 3 hours at about 1000° F. (about 538° C.)). This can result in self-bound catalyst. Based on the exchange with ammonium nitrate and subsequent calcinations in air, the ZSM-5 crystals in such a self-bound catalyst can correspond to ZSM-5 with primarily hydrogen atoms at the ion exchange sites in the zeolite. Thus, such a self-bound catalyst is sometimes described as being a self-bound catalyst that can include H-ZSM-5.

To form a transition metal-enhanced catalyst, a self-bound catalyst as described above can be impregnated via incipient wetness with a solution containing the desired metal for impregnation, such as Zn and/or Cd. (Other methods for incorporating a transition metal into the catalyst, such as ion exchange, can be used in place of or in addition to such an impregnation.) The impregnated crystal can then be dried overnight (for about 8-16 hours at about 250° F. (about 121° C.)), followed by calcination in air (for about 3 hours at about 1000° F. (about 538° C.)). More generally, a transition metal can be incorporated into the ZSM-5 crystals and/or catalyst at any convenient time, such as before or after ion exchange to form H-ZSM-5 crystals, or before or after formation of a self-bound extrudate.

As an alternative to forming self-bound catalysts, zeolite crystals can be combined with a binder to form bound catalyst compositions containing a relatively small amount of binder. Suitable binders for zeolite-based catalysts can include various inorganic oxides, such as silica, alumina, zirconia, titania, silica-alumina, cerium oxide, magnesium oxide, or combinations thereof. Generally, a binder can be present in an amount of 0 to about 80 wt %, ≤about 65 wt %, ≤about 40 wt %, ≤about 35 wt %, ≤about 25 wt %, or ≤20 wt %, based on the total weight of the catalyst composition. Additionally or alternatively, the binder may in any embodiment be present in an amount of 0 wt. %, ≥about 1.0 wt %, ≥about 5.0 wt %, ≥about 10 wt %, or ≥about 15 wt %, e.g., 0 to about 80 wt %, about 5.0 to about 40 wt %, about 10 to about 35, about 10 to about 25, or about 15 to about 20 wt %. In any embodiment, only a relatively small amount of binder may be present, e.g., an upper limit of about 5.0 wt %, about 2.5 wt %, or about 1.0 wt % and a lower limit of about 0.1 wt %, about 0.5 wt %, about 1.0 wt %, such as 0.1 to 5.0 wt %, 0.5 to 2.5 wt %, 0.5 to 1.0 wt %, or 0.1 to 1.0 wt %. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

In some aspects, a binder can be used that is substantially free of alumina, such as a binder that is essentially free of alumina. In this description, a binder that is substantially free of alumina is defined as a binder than contains ≤about 10 wt % alumina, such as ≤about 7.0 wt %, ≤about 5.0 wt %, or ≤about 3.0 wt %. A binder that is essentially free of alumina is defined as a binder that contains ≤about 1.0 wt %, such as about ≤0.5 wt %, or ≤about 0.1 wt %. Additionally or alternatively, a binder can be used that contains no intentionally added alumina and/or that contains no alumina within conventional detection limits for determining the composition of the binder and/or the reagents for forming the binder. Although alumina is commonly used as a binder for zeolite catalysts, due in part to ease of formulation of alumina-bound catalysts, in some aspects the presence of alumina in the binder can reduce and/or inhibit the activity of a catalyst composition for converting methanol to aromatics. For example, for a catalyst where the Group 10-12 and/or Group 15 is incorporated into the catalyst after formulation of the bound catalyst (such as by extrusion), the Group 10-12 and/or Group 15 element may have an affinity for exposed alumina surfaces relative to exposed zeolite surfaces, leading to increased initial deposition and/or migration of such elements to regions of the bound catalyst with an alumina surface in favor of regions with a zeolite surface. Additionally or alternatively, alumina-bound catalysts can tend to have low micropore surface area, meaning that the amount of available zeolite surface available for receiving a Group 10-12 element and/or Group 15 element may be undesirably low.

In some aspects, a binder for formulating a catalyst can be selected so that the resulting bound catalyst has a micropore surface area of at least about 3400 $m^2/g$, such as at least about 350 $m^2/g$ or at least about 370 $m^2/g$ or at least about 290 $m^2/g$, such as at least about 300 $m^2/g$ or at least about 310 $m^2/g$. Examples of a suitable binder for forming bound catalysts with a desirable micropore surface area is an alumina or silica binder. Optionally but preferably, a suitable binder can be a binder with a surface area of about 200 $m^2/g$ or less, such as about 175 $m^2/g$ or less or about 150 $m^2/g$ or less. Without being bound by any particular theory, it is believed that catalysts formed using high surface area binders (such as high surface area alumina binders) can have an increased tendency for deposited added element(s) to migrate to the binder, rather than remaining associated with the zeolite. Unless otherwise specified, the surface area of the binder is defined herein as the combined micropore surface area and mesopore surface area of the binder.

As an example of forming a bound catalyst, the following procedure describes a representative method for forming alumina bound ZSM-5 catalyst particles. ZSM-5 crystal and an alumina binder, such as an alumina binder having a surface area of about 200 $m^2/g$ or less, can be added to a mixer and mulled. Additional deionized water can be added during mulling to achieve a desired solids content for extrusion. Optionally, a caustic solution can also be added to the mixture and mulled. The mixture can then be extruded into a desired shape, such as ~1/10" quadralobes. The extrudates can be dried overnight (for about 8-16 hours at about 250° F. (about 121° C.)) and then calcined in nitrogen (for about 3 hours at about 1000° F. (about 538° C.)). The extrudates can then be exchanged twice with (an ~1N solution of) ammonium nitrate. The exchanged crystal can be dried overnight (for about 8-16 hours at about 250° F. (about 121° C.)) and then calcined in air (for about 3 hours at about 1000° F. (about 538° C.)). This can result in an alumina bound catalyst. Based on the exchange with ammonium nitrate and subsequent calcinations in air, the ZSM-5 crystals in such a bound catalyst can correspond to ZSM-5 with primarily hydrogen atoms at the ion exchange sites in the zeolite. Thus, such a bound catalyst is sometimes described as being a bound catalyst that can include H-ZSM-5.

To form a transition metal-enhanced catalyst, a bound catalyst can be impregnated via incipient wetness with a solution containing the desired metal for impregnation, such as Zn and/or Cd. The impregnated crystal can then be dried overnight (for about 8-16 hours at about 250° F. (about 121° C.)), followed by calcination in air (for about 3 hours at about 1000° F. (about 538° C.)). More generally, a transition metal can be incorporated into the ZSM-5 crystals and/or catalyst at any convenient time, such as before or after ion exchange to form H-ZSM-5 crystals, or before or after formation of a bound extrudate. In some aspects that can be preferred from a standpoint of facilitating manufacture of a bound zeolite catalyst, the transition metal can be incorporated into the bound catalyst (such as by impregnation or ion exchange) after formation of the bound catalyst by extrusion or another convenient method.

Additionally or alternatively, the invention can include one or more of the following embodiments.

Embodiment 1. A process for converting an oxygenate feedstock to olefins comprising: (a) feeding the oxygenate feedstock to a fluidized bed reactor under conditions to convert the oxygenate feedstock to a hydrocarbon mixture in a reactor effluent, wherein the fluid bed reactor comprises: (i) a catalyst; and (ii) at least one packing layer; (b) cooling the reactor effluent comprising the hydrocarbon mixture and condensing a portion of the reactor effluent to form a mixed phase effluent; (c) separating the mixed phase effluent into an aqueous liquid phase, a hydrocarbon gas phase and a hydrocarbon liquid phase; (d) separating olefins from the hydrocarbon gas phase and the hydrocarbon liquid phase.

Embodiment 2. A process for converting an oxygenate feedstock to aromatics comprising: (a) feeding the oxygenate feedstock to a fluidized bed reactor under conditions to convert the oxygenate feedstock to a hydrocarbon mixture in a reactor effluent, wherein the fluid bed reactor comprises: (i) a catalyst; and (ii) at least one packing layer; (b) cooling the reactor effluent comprising the hydrocarbon mixture and condensing a portion of the reactor effluent to form a mixed phase effluent; (c) separating the mixed phase effluent into an aqueous liquid phase, a hydrocarbon gas phase and a hydrocarbon liquid phase; and (d) separating aromatics from the hydrocarbon gas phase and the hydrocarbon liquid phase.

Embodiment 3. The process of embodiment 1 or 2, wherein the temperature in the fluidized bed reactor is about 500° F. to about 1100° F., and/or wherein the pressure in the fluidized bed reactor is about 3 psig to about 450 psig.

Embodiment 4. The process of any one of the previous embodiments, wherein the catalyst comprises a zeolite such as ZSM-5.

Embodiment 5. The process of any one of the previous embodiments, wherein the oxygenate feedstock comprises or is methanol and/or dimethylether.

Embodiment 6.

The process of claim any one of the previous embodiments, wherein the fluidized bed reactor comprises at least two packing layers.

Embodiment 7. A process for converting an oxygenate feedstock to olefins comprising: (a) feeding the oxygenate feedstock to a fluidized bed reactor under conditions to convert the oxygenate feedstock to a hydrocarbon mixture comprising olefins in a reactor effluent, wherein the fluidized bed reactor comprises: (i) a catalyst; and (ii) two packing layers, which separate the fluidized bed reactor into two stages; (b) cooling the fluidized bed reactor either internally or externally; (c) transferring spent catalyst comprising coke to an air stream in fluid connection with the fluidized bed reactor and a regenerator; (d) feeding the air stream containing spent catalyst to the regenerator and burning the coke off of the catalyst to form regenerated catalyst; and (e) transferring the regenerated catalyst from the regenerator to the fluidized bed reactor, wherein the regenerator is in fluid connection with the fluidized bed reactor.

Embodiment 8. The process of embodiment 7, wherein the fluidized bed reactor is cooled internally with a heat exchanger in each stage.

Embodiment 9. The process of embodiment 7 or 8, wherein the fluidized bed reactor is cooled externally with a catalyst cooler in fluid connection with the fluidized bed reactor.

Embodiment 10. The process of any one of embodiments 7-9, further comprising feeding a gas recycle stream into the fluidized bed reactor or combining the gas recycle stream with the oxygenate feedstock.

Embodiment 11. The process of any one of embodiments 7-10, wherein the oxygenate feedstock is selected from the group consisting of methanol, dimethylether, and a combination thereof.

Embodiment 12. A process for converting an oxygenate feedstock to olefins comprising: (a) heating the oxygenate feedstock; (b) feeding the oxygenate feedstock to a fluidized bed reactor under conditions to convert the oxygenate feedstock to a hydrocarbon mixture comprising olefins in a reactor effluent, wherein the fluidized bed reactor comprises: (i) a catalyst; and (ii) two packing layers, which separate the fluidized bed reactor into two stages; (c) cooling the fluidized bed reactor either internally or externally; (d) transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other; (e) transferring the reactor effluent to a heat exchanger for cooling the reactor effluent and condensing a portion of the reactor effluent against incoming oxygenate feed to form a mixed phase effluent, wherein the heat exchanger is in fluid connection with the fines collection unit or the set of two stage cyclones; (f) transferring the mixed phase effluent to a separator in fluid connection with the heat exchanger and separating the mixed phase effluent into an aqueous liquid phase, a hydrocarbon gas phase and a hydrocarbon liquid phase; (g) transferring the hydrocarbon gas phase and the hydrocarbon liquid phase to a stabilizer/de-butanizer in fluid connection with the separator, wherein at least olefins are separated; (h) optionally, recycling a portion of the olefins; (j) transferring spent catalyst comprising coke to an air stream in fluid connection with the fluidized bed reactor and a regenerator; (k) feeding the air stream containing spent catalyst to the regenerator and burning the coke off of the catalyst to form regenerated catalyst; and (m) transferring the regenerated catalyst from the regenerator to the fluidized bed reactor, wherein the regenerator is in fluid connection with the fluidized bed reactor.

Embodiment 13. The process of embodiment 12, further comprising cooling the mixed phase effluent before transferring the mixed phase effluent to the separator.

Embodiment 14. The process of embodiment 12 or 13, further comprising feeding a recycle stream comprising a portion of the olefins to the fluidized bed reactor, wherein the recycle stream is in fluid connection with the stabilizer and the fluidized bed reactor.

Embodiment 15. The process of any one of embodiments 12-14, further comprising: (n) feeding a recycle stream comprising a portion of the olefins to a second reactor in fluid connection with the stabilizer to produce a second hydrocarbon mixture in a second reactor effluent; (o) transferring the second reactor effluent to a second set of two stage cyclones for separating reactor vapor from the catalyst and/or transferring the second reactor effluent to a second fines collection unit for removing catalyst fines, wherein the second set of two stage cyclones and the second fines collection unit are in fluid connection with the second reactor and/or each other; (p) transferring the second reactor effluent to a second cooler and cooling the second reactor effluent and condensing a portion of the second reactor effluent to form a second mixed phase effluent, wherein the second cooler is in fluid connection with the second fines collection unit or the second set of two stage cyclones; (q) transferring the second mixed phase effluent to a second separator in fluid connection with the second cooler and separating the second mixed phase effluent into a second aqueous liquid phase, a second hydrocarbon gas phase and a second hydrocarbon liquid phase; and (r) mixing the at least one of the second hydrocarbon gas phase and the hydrocarbon liquid phase with at least one stream from the stabilizer to form a combined mixture and separating at least olefins from the combined mixture in one or more steps.

Embodiment 16. The process of embodiment 15, wherein the second reactor is a second fluidized bed reactor comprising the catalyst and further comprises: (s) cooling the second fluidized bed reactor internally with a second reactor heat exchanger; (t) transferring spent catalyst comprising coke from the second fluidized bed reactor to the air stream in fluid connection with the fluidized bed reactor, the second fluidized bed reactor and the regenerator; (u) feeding the air stream containing spent catalyst to the regenerator and burning the coke off of the catalyst to form regenerated catalyst; and (v) transferring the regenerated catalyst from the regenerator to the second fluidized bed reactor, wherein the regenerator is in fluid connection with fluidized bed reactor and the second fluidized bed reactor.

Embodiment 17. The process of embodiment 15 or 16, wherein the fluidized bed reactor is cooled internally with a heat exchanger in each stage.

Embodiment 18. The process of any one of embodiments 12-17, wherein the fluidized bed reactor is cooled externally with the catalyst cooler in fluid connection with the fluidized bed reactor.

Embodiment 19. A process for converting an oxygenate feedstock to olefins comprising: (a) heating the oxygenate feedstock; (b) feeding the oxygenate feedstock to a fluidized bed reactor under conditions to convert the oxygenate feedstock to a hydrocarbon mixture comprising olefins in a reactor effluent, wherein the fluidized bed reactor comprises: (i) a catalyst; and (ii) two packing layers, which separate the fluidized bed reactor into two stages; (c) cooling the fluidized bed reactor either internally or externally; (d) transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other; (e) transferring the reactor effluent to a heat exchanger for cooling the reactor effluent and condensing at least a portion of the reactor effluent against incoming oxygenate feed to form a mixed phase effluent, wherein the heat exchanger is in fluid connection with the fines collection unit or the set of two stage cyclones; (f) transferring the mixed phase effluent to a separator in fluid connection with the heat exchanger and separating the mixed phase effluent into an aqueous liquid phase, a hydrocarbon gas phase and a hydrocarbon liquid phase; (g) transferring the hydrocarbon gas phase and the hydrocarbon liquid phase to a de-ethanizer in fluid connection with the separator, wherein at least $C_2-$ light gas is separated from $C_{3+}$ product; (h) transferring the $C_{3+}$ product to a de-butanizer in fluid connection with the de-ethanizer, wherein at least olefins are separated; and (j) optionally, transferring the olefins to an alkylation unit in fluid connection with the de-butanizer.

Embodiment 20. A process for converting an oxygenate feedstock to olefins comprising: (a) heating the oxygenate feedstock; (b) feeding the oxygenate feedstock to a fluidized bed reactor under conditions to convert the oxygenate feedstock to a hydrocarbon mixture comprising olefins in a reactor effluent, wherein the fluid bed reactor comprises: (i) a catalyst; and (ii) two packing layers, which separate the fluidized bed reactor into two stages; (c) cooling the fluidized bed reactor either internally or externally; (d) transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other; (e) transferring the reactor effluent to a heat exchanger for cooling the reactor effluent and condensing at least a portion of the reactor effluent against incoming oxygenate feed to form a mixed phase effluent, wherein the heat exchanger is in fluid connection with the fines collection unit or the set of two stage cyclones; (f) transferring the mixed phase effluent to a separator in fluid connection with the heat exchanger and separating the mixed phase effluent into an aqueous liquid phase, a hydrocarbon gas phase and a hydrocarbon liquid phase; (g) transferring the hydrocarbon gas phase and the hydrocarbon liquid phase to a dividing wall column in fluid connection with the separator, wherein at least streams for a light gas, $C_2$, propylene, propane, butenes, butanes and the $C_{5+}$ gasoline product are produced; (h) combining the streams for $C_2$, propylene, and butenes to form an olefin stream in fluid connection with the dividing wall column; (j) optionally, combining the streams for propane and butanes to form an LPG stream; and (k) optionally, recycling the olefin stream to the fluidized bed reactor, wherein the olefin stream is in fluid connection with the dividing wall column and the fluidized bed reactor.

Embodiment 21. The process of embodiment 20, wherein the hydrocarbon gas phase and the hydrocarbon liquid phase are transferred by a pump to the dividing wall column.

Embodiment 22. A process for converting an oxygenate feedstock to aromatics comprising: (a) feeding the oxygenate feedstock to a fluidized bed reactor under conditions to convert the oxygenate feedstock to a hydrocarbon mixture comprising aromatics in a reactor effluent, wherein the fluidized bed reactor comprises: (i) a catalyst; and (ii) two packing layers, which separate the fluidized bed reactor into two stages; (b) cooling the fluidized bed reactor either internally or externally; (c) transferring spent catalyst comprising coke to an air stream in fluid connection with the fluidized bed reactor and a regenerator; (d) feeding the air stream containing spent catalyst to the regenerator and burning the coke off of the catalyst to form regenerated catalyst; and (e) transferring the regenerated catalyst from the regenerator to the fluidized bed reactor, wherein the regenerator is in fluid connection with the fluidized bed reactor.

Embodiment 23. The process of embodiment 22, wherein the fluidized bed reactor is cooled internally with a heat exchanger in each stage.

Embodiment 24. The process of embodiment 22 or 23, wherein the fluidized bed reactor is cooled externally with a catalyst cooler in fluid connection with the fluidized bed reactor.

Embodiment 25. The process of any one of embodiments 22-24, further comprising feeding a gas recycle stream into the fluidized bed reactor or combining the gas recycle stream with the oxygenate feedstock.

Embodiment 26. The process of any one of embodiments 22-25, wherein the oxygenate feedstock comprises or is methanol and/or dimethylether.

Embodiment 27. A process for converting an oxygenate feedstock to aromatics comprising: (a) heating the oxygenate feedstock; (b) feeding the oxygenate feedstock to a fluidized bed reactor under conditions to convert the oxygenate feedstock to a hydrocarbon mixture comprising aromatics in a reactor effluent, wherein the fluidized bed reactor comprises: (i) a catalyst; and (ii) two packing layers, which separate the fluidized bed reactor into two stages; (c) cooling the fluidized bed reactor either internally or externally; (d) transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other; (e) transferring the reactor effluent to a heat exchanger for cooling the reactor effluent and condensing a portion of the reactor effluent against incoming oxygenate feed to form a mixed phase effluent, wherein the heat exchanger is in fluid connection with the fines collection unit or the set of two stage cyclones; (f) transferring the mixed phase effluent to a separator in fluid connection with the heat exchanger and separating the mixed phase effluent into an aqueous liquid phase, a hydrocarbon gas phase and a hydrocarbon liquid phase; (g) transferring the hydrocarbon gas phase and the hydrocarbon liquid phase to a stabilizer/de-butanizer in fluid connection with the separator, wherein at least aromatics are separated; (h) optionally, recycling olefins; (j) transferring spent catalyst comprising coke to an air stream in fluid connection with the fluidized bed reactor and a regenerator; (k) feeding the air stream containing spent catalyst to the regenerator and burning the coke off of the catalyst to form regenerated catalyst; and (m) transferring the regenerated catalyst from the regenerator to the fluidized bed reactor, wherein the regenerator is in fluid connection with the fluidized bed reactor.

Embodiment 28. The process of embodiment 27, further comprising cooling the mixed phase effluent before transferring the mixed phase effluent to the separator, wherein the cooler is in fluid connection with the heat exchanger and the separator.

Embodiment 29. The process of embodiment 27 or 28, further comprising feeding a recycle stream comprising olefins to the fluidized bed reactor, wherein the recycle stream is in fluid connection with the stabilizer and the fluidized bed reactor.

Embodiment 30. The process of any one of embodiments 27-29, further comprising: (n) feeding a recycle stream to a second reactor in fluid connection with the stabilizer to produce a second hydrocarbon mixture in a second reactor effluent; (o) transferring the second reactor effluent to a second set of two stage cyclones for separating reactor vapor from the catalyst and/or transferring the second reactor effluent to a second fines collection unit for removing catalyst fines, wherein the second set of two stage cyclones and the second fines collection unit are in fluid connection with the second reactor and/or each other; (p) transferring the second reactor effluent to a second cooler and cooling the second reactor effluent and condensing a portion of the second reactor effluent to form a second mixed phase effluent, wherein the second cooler is in fluid connection with the second fines collection unit or the second set of two stage cyclones; (q) transferring the second mixed phase effluent to a second separator in fluid connection with the second cooler and separating the second mixed phase effluent into a second aqueous liquid phase, a second hydrocarbon gas phase and a second hydrocarbon liquid phase; and (r) mixing the at least one of the second hydrocarbon gas phase and the hydrocarbon liquid phase with at least one stream from the stabilizer to form a combined mixture and separating at least aromatics from the combined mixture in one or more steps.

Embodiment 31. The process of embodiment 30, wherein the second reactor is a second fluidized bed reactor comprising the catalyst and further comprises: (s) cooling the second fluidized bed reactor internally with a second reactor heat exchanger; (t) transferring spent catalyst comprising coke from the second fluidized bed reactor to the air stream in fluid connection with the fluidized bed reactor, the second fluidized bed reactor and the regenerator; (u) feeding the air stream containing spent catalyst to the regenerator and burning the coke off of the catalyst to form regenerated catalyst; and (v) transferring the regenerated catalyst from the regenerator to the second fluidized bed reactor, wherein the regenerator is in fluid connection with fluidized bed reactor and the second fluidized bed reactor.

Embodiment 32 The process of embodiment 30 or 31, wherein the fluidized bed reactor is cooled internally with a heat exchanger in each stage.

Embodiment 33. The process of any one of embodiments 27-32, wherein the fluidized bed reactor is cooled externally with the catalyst cooler in fluid connection with the fluidized bed reactor.

Embodiment 34. A process for converting an oxygenate feedstock to aromatics comprising: (a) heating the oxygenate feedstock; (b) feeding the oxygenate feedstock to a fluidized bed reactor under conditions to convert the oxygenate feedstock to a hydrocarbon mixture comprising aromatics in a reactor effluent, wherein the fluidized bed reactor comprises: (i) a catalyst; and (ii) two packing layers, which separate the fluidized bed reactor into two stages; (c) cooling the fluidized bed reactor either internally or externally; (d) transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other; (e) transferring the reactor effluent to a heat exchanger for cooling the reactor effluent and condensing at least a portion of the reactor effluent against incoming oxygenate feed to form a mixed phase effluent, wherein the heat exchanger is in fluid connection with the fines collection unit or the set of two stage cyclones; (f) transferring the mixed phase effluent to a separator in fluid connection with the heat exchanger and separating the mixed phase effluent into an aqueous liquid phase, a hydrocarbon gas phase and a hydrocarbon liquid phase; (g) transferring the hydrocarbon gas phase and the hydrocarbon liquid phase to at least one stabilizer in fluid connection with the separator and separating at least aromatics in one or more steps; and (h) optionally, separating olefins and transferring the olefins to an alkylation unit in fluid connection with the stabilizer.

Embodiment 35. A process for converting an oxygenate feedstock to aromatics comprising: (a) heating the oxygenate feedstock; (b) feeding the oxygenate feedstock to a fluidized bed reactor under conditions to convert the oxygenate feedstock to a hydrocarbon mixture comprising aromatics in a reactor effluent, wherein the fluid bed reactor comprises: (i) a catalyst; and (ii) two packing layers, which separate the fluidized bed reactor into two stages; (c) cooling the fluidized bed reactor either internally or externally; (d) transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other; (e) transferring the reactor effluent to a heat exchanger for cooling the reactor effluent and condensing at least a portion of the reactor effluent against incoming oxygenate feed to form a mixed phase effluent, wherein the heat exchanger is in fluid connection with the fines collection unit or the set of two stage cyclones; (f) transferring the mixed phase effluent to a separator in fluid connection with the heat exchanger and separating the mixed phase effluent into an aqueous liquid phase, a hydrocarbon gas phase and a hydrocarbon liquid phase; (g) transferring the hydrocarbon gas phase and the hydrocarbon liquid phase to a dividing wall column in fluid connection with the separator, wherein at least one stream comprising aromatics is produced; (h) optionally, producing a light gas, $C_2$, propylene, propane, butenes, butanes and $C_{5+}$ gasoline product streams; (j) optionally, combining the streams for $C_2$, propylene, and butenes to form an olefin stream in fluid connection with the dividing wall column; (k) optionally, combining the streams for propane and butanes to form an LPG stream; and (m) optionally, recycling an olefin stream to the fluidized bed reactor, wherein the olefin stream is in fluid connection with the dividing wall column and the fluidized bed reactor.

Embodiment 36. The process of embodiment 35, wherein the hydrocarbon gas phase and the hydrocarbon liquid phase are transferred by a pump to the dividing wall column.

What is claimed is:

1. A process for converting an oxygenate feedstock to olefins comprising:
   a. heating the oxygenate feedstock;
   b. feeding the oxygenate feedstock to a fluidized bed reactor under conditions to convert the oxygenate feedstock to a hydrocarbon mixture comprising olefins in a reactor effluent, wherein the fluidized bed reactor comprises:
      i. a catalyst; and
      ii. two packing layers, which separate the fluidized bed reactor into two stages;
   c. cooling the fluidized bed reactor either internally or externally;
   d. transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other;
   e. transferring the reactor effluent to a heat exchanger for cooling the reactor effluent and condensing a portion of the reactor effluent against incoming oxygenate feed to form a mixed phase effluent, wherein the heat exchanger is in fluid connection with the fines collection unit or the set of two stage cyclones;
   f. transferring the mixed phase effluent to a separator in fluid connection with the heat exchanger and separating the mixed phase effluent into an aqueous liquid phase, a hydrocarbon gas phase and a hydrocarbon liquid phase;
   g. transferring the hydrocarbon gas phase and the hydrocarbon liquid phase to a stabilizer/de-butanizer in fluid connection with the separator, wherein at least olefins are separated;
   h. optionally, recycling a portion of the olefins;
   i. transferring spent catalyst comprising coke to an air stream in fluid connection with the fluidized bed reactor and a regenerator;
   j. feeding the air stream containing spent catalyst to the regenerator and burning the coke off of the catalyst to form regenerated catalyst; and
   k. transferring the regenerated catalyst from the regenerator to the fluidized bed reactor, wherein the regenerator is in fluid connection with the fluidized bed reactor;
   l. feeding a recycle stream comprising a portion of the olefins to a second reactor in fluid connection with the stabilizer to produce a second hydrocarbon mixture in a second reactor effluent;
   m. transferring the second reactor effluent to a second set of two stage cyclones for separating reactor vapor from the catalyst and/or transferring the second reactor effluent to a second fines collection unit for removing catalyst fines, wherein the second set of two stage cyclones and the second fines collection unit are in fluid connection with the second reactor and/or each other;
   n. transferring the second reactor effluent to a second cooler and cooling the second reactor effluent and condensing a portion of the second reactor effluent to form a second mixed phase effluent, wherein the second cooler is in fluid connection with the second fines collection unit or the second set of two stage cyclones;
   o. transferring the second mixed phase effluent to a second separator in fluid connection with the second cooler and separating the second mixed phase effluent into a second aqueous liquid phase, a second hydrocarbon gas phase and a second hydrocarbon liquid phase; and
   p. mixing the at least one of the second hydrocarbon gas phase and the hydrocarbon liquid phase with at least one stream from the stabilizer to form a combined mixture and separating at least olefins from the combined mixture in one or more steps
   q. cooling the second fluidized bed reactor internally with a second reactor heat exchanger;
   r. transferring spent catalyst comprising coke from the second fluidized bed reactor to the air stream in fluid connection with the fluidized bed reactor, the second fluidized bed reactor and the regenerator;
   s. feeding the air stream containing spent catalyst to the regenerator and burning the coke off of the catalyst to form regenerated catalyst and
   t. transferring the regenerated catalyst from the regenerator to the second fluidized bed reactor, wherein the regenerator is in fluid connection with fluidized bed reactor and the second fluidized bed reactor.

2. The process of claim 1, further comprising cooling the mixed phase effluent before transferring the mixed phase effluent to the separator.

3. The process of claim 1, further comprising feeding a recycle stream comprising a portion of the olefins to the fluidized bed reactor, wherein the recycle stream is in fluid connection with the stabilizer and the fluidized bed reactor.

4. The process of claim 1, wherein the fluidized bed reactor is cooled internally with a heat exchanger in each stage.

5. The process of any one of the preceding claims, wherein the fluidized bed reactor is cooled externally with the catalyst cooler in fluid connection with the fluidized bed reactor.

6. A process for converting an oxygenate feedstock to aromatics comprising:
   a. heating the oxygenate feedstock;
   b. feeding the oxygenate feedstock to a fluidized bed reactor under conditions to convert the oxygenate feedstock to a hydrocarbon mixture comprising aromatics in a reactor effluent, wherein the fluidized bed reactor comprises:
      i. a catalyst; and
      ii. two packing layers, which separate the fluidized bed reactor into two stages;
   c. cooling the fluidized bed reactor either internally or externally;
   d. transferring the reactor effluent to a set of two stage cyclones for separating reactor vapor from the catalyst and/or transferring the reactor effluent to a fines collection unit for removing catalyst fines, wherein the set of two stage cyclones and the fines collection unit are in fluid connection with the fluidized bed reactor and/or each other;
   e. transferring the reactor effluent to a heat exchanger for cooling the reactor effluent and condensing a portion of the reactor effluent against incoming oxygenate feed to form a mixed phase effluent, wherein the heat exchanger is in fluid connection with the fines collection unit or the set of two stage cyclones;

f. transferring the mixed phase effluent to a separator in fluid connection with the heat exchanger and separating the mixed phase effluent into an aqueous liquid phase, a hydrocarbon gas phase and a hydrocarbon liquid phase;
g. transferring the hydrocarbon gas phase and the hydrocarbon liquid phase to a stabilizer/de-butanizer in fluid connection with the separator, wherein at least aromatics are separated;
h. optionally, recycling olefins;
i. transferring spent catalyst comprising coke to an air stream in fluid connection with the fluidized bed reactor and a regenerator;
j. feeding the air stream containing spent catalyst to the regenerator and burning the coke off of the catalyst to form regenerated catalyst; and
k. transferring the regenerated catalyst from the regenerator to the fluidized bed reactor, wherein the regenerator is in fluid connection with the fluidized bed reactor;
l. feeding a recycle stream to a second reactor in fluid connection with the stabilizer to produce a second hydrocarbon mixture in a second reactor effluent;
m. transferring the second reactor effluent to a second set of two stage cyclones for separating reactor vapor from the catalyst and/or transferring the second reactor effluent to a second fines collection unit for removing catalyst fines, wherein the second set of two stage cyclones and the second fines collection unit are in fluid connection with the second reactor and/or each other;
n. transferring the second reactor effluent to a second cooler and cooling the second reactor effluent and condensing a portion of the second reactor effluent to form a second mixed phase effluent, wherein the second cooler is in fluid connection with the second fines collection unit or the second set of two stage cyclones;
o. transferring the second mixed phase effluent to a second separator in fluid connection with the second cooler and separating the second mixed phase effluent into a second aqueous liquid phase, a second hydrocarbon gas phase and a second hydrocarbon liquid phase; and
p. mixing the at least one of the second hydrocarbon gas phase and the hydrocarbon liquid phase with at least one stream from the stabilizer to form a combined mixture and separating at least aromatics from the combined mixture in one or more steps;
q. cooling the second fluidized bed reactor internally with a second reactor heat exchanger;
r. transferring spent catalyst comprising coke from the second fluidized bed reactor to the air stream in fluid connection with the fluidized bed reactor, the second fluidized bed reactor and the regenerator;
s. feeding the air stream containing spent catalyst to the regenerator and burning the coke off of the catalyst to form regenerated catalyst and
t. transferring the regenerated catalyst from the regenerator to the second fluidized bed reactor, wherein the regenerator is in fluid connection with fluidized bed reactor and the second fluidized bed reactor;
wherein the fluidized bed reactor is cooled internally with a heat exchanger in each stage.

7. The process of claim 6, further comprising cooling the mixed phase effluent before transferring the mixed phase effluent to the separator, wherein the cooler is in fluid connection with the heat exchanger and the separator.

8. The process of claim 6, further comprising feeding a recycle stream comprising olefins to the fluidized bed reactor, wherein the recycle stream is in fluid connection with the stabilizer and the fluidized bed reactor.

9. The process of any one of the preceding claims, wherein the fluidized bed reactor is cooled externally with the catalyst cooler in fluid connection with the fluidized bed reactor.

* * * * *